United States Patent
Zhang et al.

(10) Patent No.: US 10,597,687 B2
(45) Date of Patent: Mar. 24, 2020

(54) BIOSYNTHETIC PATHWAYS AND PRODUCTS

(71) Applicant: REGENTS OF THE UNIVERSITY OF MINNESOTA, Minneapolis, MN (US)

(72) Inventors: Kechun Zhang, Roseville, MN (US); Mingyong Xiong, Manitowoc, WI (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 16/252,054

(22) Filed: Jan. 18, 2019

(65) Prior Publication Data

US 2019/0153490 A1    May 23, 2019

Related U.S. Application Data

(62) Division of application No. 14/783,375, filed as application No. PCT/US2014/034588 on Apr. 18, 2014, now Pat. No. 10,202,624.

(60) Provisional application No. 61/813,354, filed on Apr. 18, 2013, provisional application No. 61/866,233, filed on Aug. 15, 2013.

(51) Int. Cl.
| | |
|---|---|
| *C07D 309/30* | (2006.01) |
| *C12P 17/06* | (2006.01) |
| *C12P 7/42* | (2006.01) |
| *C12N 9/10* | (2006.01) |
| *C07D 309/32* | (2006.01) |
| *C07D 309/38* | (2006.01) |

(52) U.S. Cl.
CPC .......... *C12P 17/06* (2013.01); *C07D 309/30* (2013.01); *C07D 309/32* (2013.01); *C07D 309/38* (2013.01); *C12N 9/1025* (2013.01); *C12N 9/1029* (2013.01); *C12P 7/42* (2013.01)

(58) Field of Classification Search
CPC .......... C12P 17/06; C12P 7/42; C07D 309/38; C07D 309/30; C07D 309/32; C12N 9/1025; C12N 9/1029
USPC ........................................................ 549/292
See application file for complete search history.

(56) References Cited

U.S. PATENT DOCUMENTS

| | | | |
|---|---|---|---|
| 4,634,780 | A | 1/1987 | Alper |
| 6,428,767 | B1 | 8/2002 | Burch et al. |
| 2005/0287655 | A1 | 12/2005 | Tabata et al. |
| 2012/0277475 | A1 | 11/2012 | Couturier et al. |

OTHER PUBLICATIONS

White et al, synthesis of (+−)-Lineatin, an Aggregation Pheromone of Trypodendron Lineatum, J. Am. Chem.Soc. 1982, 104, p. 5486-5489. (Year: 1982).*

(Continued)

*Primary Examiner* — Taylor V Oh
(74) *Attorney, Agent, or Firm* — Mueting, Raasch & Gebhardt, P.A.

(57) ABSTRACT

This disclosure describes biosynthesized compounds including anhydromevalonolactone and β-methyl-δ-valerolactone. This disclosure further describes biosynthetic methods for making these compounds. In some embodiments, the biosynthetic methods can include a combination of biosynthesis and chemical steps to produce β-methyl-δ-valerolactone. Finally, this disclosure described recombinant cells useful for the biosynthesis of these compounds.

3 Claims, 11 Drawing Sheets

Specification includes a Sequence Listing.

(56) References Cited

OTHER PUBLICATIONS

International Search Report and Written Opinion for PCT/US2014/034588, issued by the European Patent Office, dated Oct. 29, 2014; 16 pgs.

International Preliminary Report on Patentability for PCT/US2014/034588, issued by The International Bureau of WIPO; dated Oct. 29, 2015; 11 pgs.

"2,3-anhydromevalonic acid" product sheet from *Comparative Toxicogenomics Database*, 2015; 1 pg.

Bougioukou et al., "Directed Evolution of an Enantioselective Enoate-Reductase: Testing the Utility of Iterative Saturation Mutagenesis," *Advanced Synthesis & Catalysis*, Dec. 2009;351(18):3287-3305.

Campobasso, "*Staphylococcus aureus* 3-hydroxy-3-methylglutaryl-CoA synthase: crystal structure and mechanism" Oct. 2004 *J Biol Chem*. 279(43):44883-8. Epub Aug. 2, 2004.

Compound Summary for CID 557445: Dehydromevalonic Lactone, Create Date: Mar. 27, 2005; Modify Date Nov. 7, 2005: 7 pgs.

Datsenko and Wanner, "One-step inactivation of chromosomal genes in *Escherichia coli* K-12 using PCR Products," *Proc Natl Acad Sci USA*, Jun. 6, 2000;97(12):6640-6645.

European Search Results for European Patent Application No. 14727665.3, dated Feb. 13, 2017; 1 page.

Grundlinger et al., "Fungal siderophore biosynthesis is partially localized in peroxisomes," *Mot Microbiol*, Jun. 2013;88(5):862-875.

Jones, "Radioactive Dating Explained" Jul. 2000, Online: http://www.scienceagainstevolution.org/v4i10f.htm. (Accessed: Jan. 21, 2018.) pp. 1-6.

Martin et al., "Engineering a mevalonate pathway in *Escherichia coli*, for production of terpenoids," *Nat Biotech*, Jul. 2003;21(7):796-802.

Naggert et al., "Cloning, sequencing, and characterization of *Escherichia coli* thioesterase II," *Journal Biol Chem*, Jun. 15, 1991;266(17):11044-11050.

Nangia et al., "Facile synthesis of Anhydromevalonolactone from Ethyl Acetoacetate," *Synthetic Communication*, 1992:22(4):593-602.

Punya et al., "Functional expression of a foreign gene in *Aspergillus oryzae* producing new pyrone compounds," *Fungal Genetics and Biology*, Jan. 1, 2013;50:55-62.

Rua et al., "Engineering *Macaca fascicularis* cytochrome P450 2C20 to reduce animal testing for new drugs," *J Inorg Biochem*, Dec. 2012;117:277-284.

Sambrook et al., *Molecular Cloning: A Laboratory Manual*, Cold Spring Harbor Laboratory Press, 1989; Cover page, table of contents only.

Shen et al., "Driving forces enable high-titer anaerobic 1-butanol synthesis in *Escherichia coli*," *Appl Environ Microbiol*, May 2011;77(9):2905-2915.

Tabata et al., "Production of mevalonate by a metabolically-engineered *Escherichia coli*," *Biotechnol Lett*, Oct. 2004;26(19):1487-1491.

Wattanchaisaereekul, S., "Assessing medium constituents for optimal heterologous production of anhydromevalonolactone in recombinant Aspergillus oryzae," *AMB Express*, Jun. 2014;4:1-16.

Xiong et al., "A bio-catalytic approach to aliphatic ketones," *Scientific Reports*, Mar. 13, 2012;2:311: 7 pgs.

Xiong et al., "Biosynthesis of Branched Hydroxyacids as Renewable Polymer Monomers" Poster, Nov. 19, 2012.

Yasmin et al., "Mevalonate governs interdependency of ergosterol and siderophore biosynthesis in the fungal pathogen *Aspergillus fumigatus*," *Proc Natl Acad Sci*, Feb. 21, 2012;109(8):E497-E504.

Nakayama, "Synthesis and degradability of a novel aliphatic polyester based on l-lactide and sorbitol: 3" 1996 Polymer, 37(4):651-660.

\* cited by examiner

BIOSYNTHETIC PATHWAYS AND PRODUCTS

CROSS-REFERENCE TO RELATED APPLICATION

This application is a divisional application of pending U.S. patent application Ser. No. 14/783,375, filed Oct. 8, 2015, which is the § 371 U.S. National Stage of International Application No. PCT/US2014/034588, filed Apr. 18, 2014, which claims priority to U.S. Provisional Patent Application Ser. No. 61/813,354, filed Apr. 18, 2013 and U.S. Provisional Patent Application Ser. No. 61/866,233, filed Aug. 15, 2013, each of which is incorporated herein by reference.

SUMMARY

This disclosure describes, in one aspect, biosynthesized compounds including anhydromevalonolactone and β-methyl-δ-valerolactone. In another aspect, this disclosure further describes biosynthetic methods for making these compounds. In some embodiments, the biosynthetic methods can include a combination of biosynthesis and chemical steps to produce β-methyl-δ-valerolactone. In yet another aspect, this disclosure described recombinant cells useful for the biosynthesis of these compounds.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
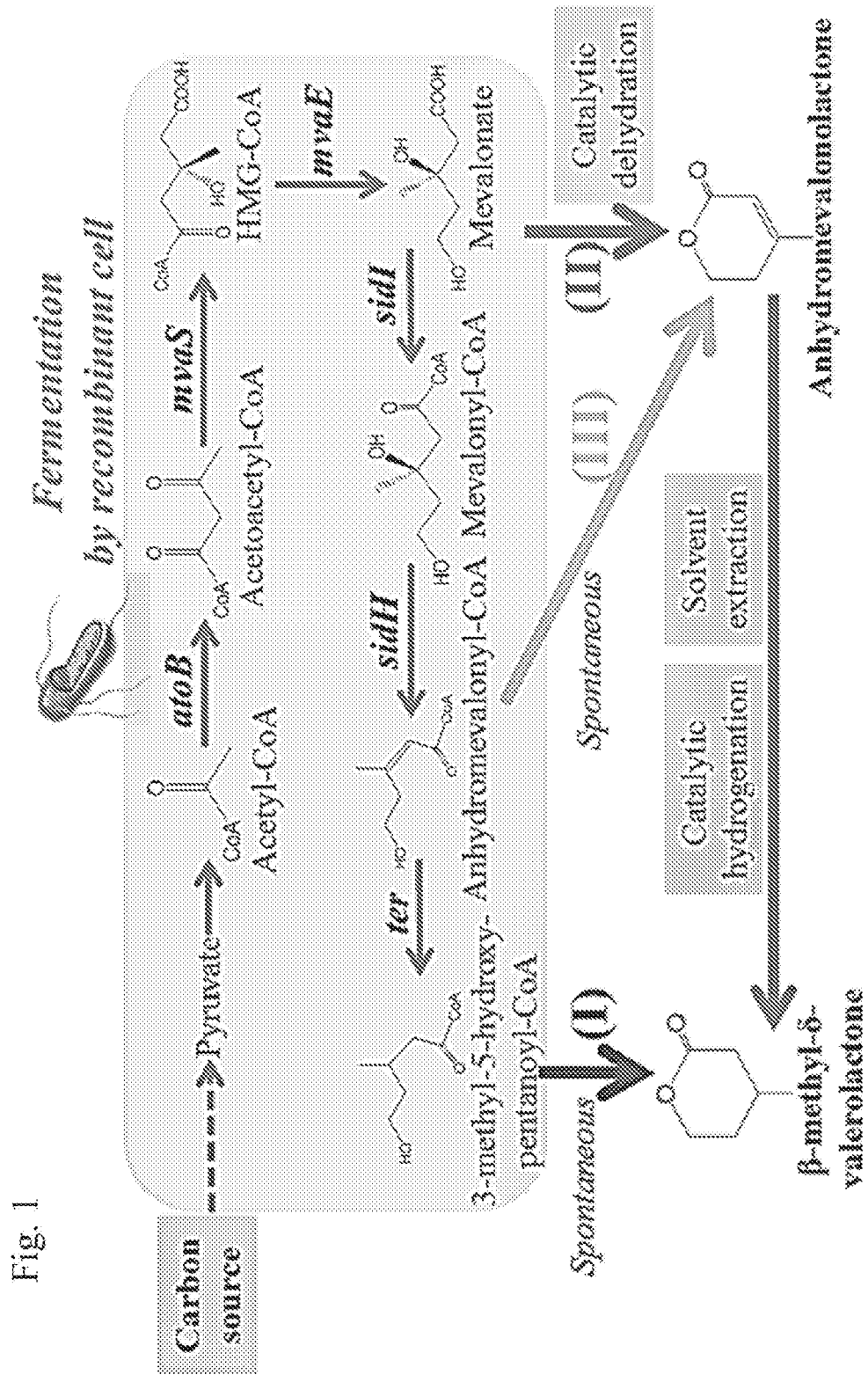
FIG. 1. Bio-based routes to β-methyl-δ-valerolactone (βMδVL). (I) Full artificial synthetic pathway. atoB: acetyl-CoA acetyltransferase; mvaS: HMG-CoA synthase; mvaE: HMG-CoA reductase; sidI: acyl-CoA ligase; sidH: enoyl-CoA hydratase; ter: enoyl-CoA reductase. (II) Hybrid pathway. Biosynthesized mevalonate is converted to βMδVL through catalytic dehydration and hydrogenation. (III) Intermediate anhydromevalonyl-CoA can spontaneously cyclize to anhydromevalonolactone.
Figure 8:
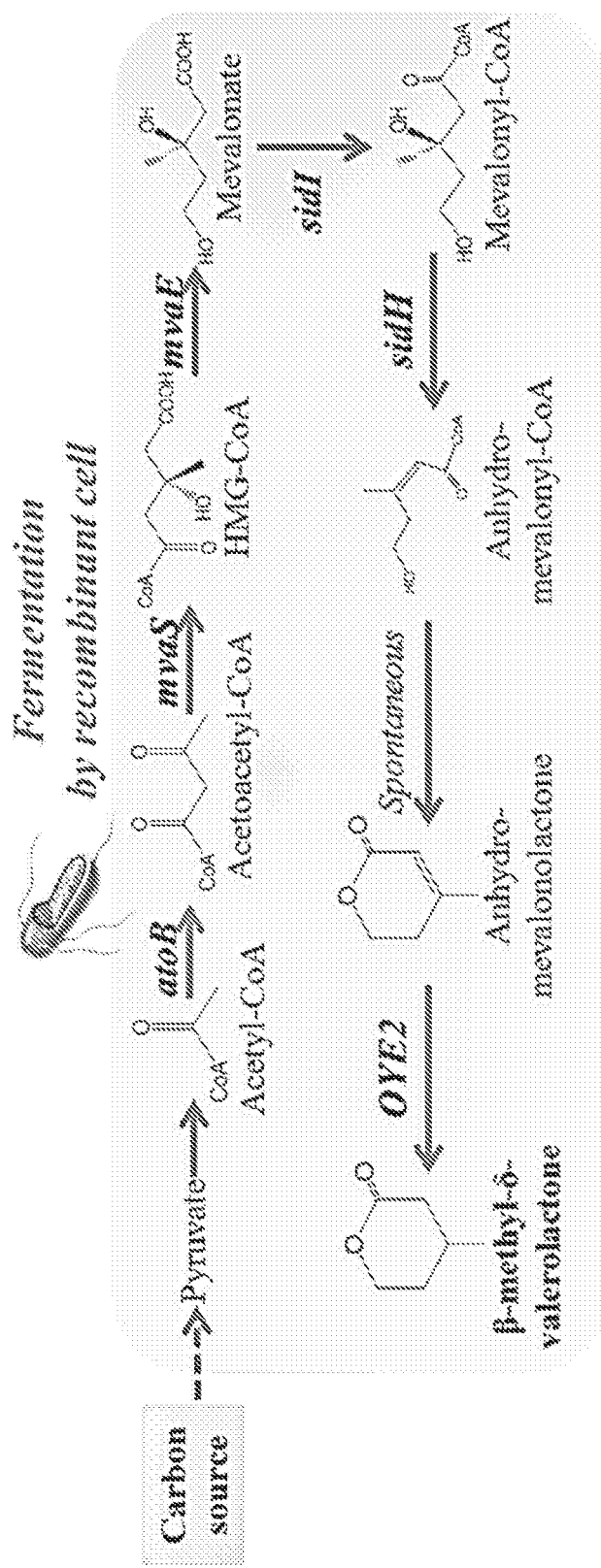
FIG. 8. Alternative bio-based routes to β-methyl-δ-valerolactone (βMδVL). atoB: acetyl-CoA acetyltransferase; mvaS: HMG-CoA synthase; mvaE: HMG-CoA reductase; sidI: acyl-CoA ligase; sidH: enoyl-CoA hydratase; OYE2: enoate-reductase.

This disclosure relates to biosynthetic pathways—and genetically modified microbes that possess those pathways—useful for the production of β-methyl-δ-valerolactone. This disclosure describes a full biosynthetic pathway to biosynthesize 3-methyl-5-hydroxypentanoyl-CoA from a renewable carbon source. As shown in FIG. 1, 3-methyl-5-hydroxypentanoyl-CoA spontaneously converts to the end product, β-methyl-δ-valerolactone. Alternatively, as shown in FIG. 8, anhydromevalonyl-CoA spontaneously cyclizes to anhydromevalonolactone, which can be reduced to β-methyl-δ-valerolactone. This disclosure also describes an integrated process to produce β-methyl-δ-valerolactone that involves conversion of either anhydromevalonyl-CoA or mevalonate to anhydromevalonolactone, then chemical processing of anhydromevalonolactone to produce β-methyl-δ-valerolactone.

Currently, polylactide (PLA) is an example of a bio-based renewable polymer that has significant market impact. However, the semi-crystalline nature of PLA has limited its applications. This disclosure describes development of an innovative fermentation processes for novel polymer monomers that can polymerize into amorphous structures.

Design and Construct a Novel Synthetic Metabolic Pathway

No naturally-existing microbial metabolic pathway produces β-methyl-δ-valerolactone directly from a carbohydrate carbon source such as, for example, glucose. We have designed and engineered non-natural metabolic pathways to β-methyl-δ-valerolactone (FIG. 1 and FIG. 8).

First, we introduced a heterologous pathway into a microbial host to produce a non-native metabolite mevalonate. (FIG. 1, Route I) The mevalonate pathway exists in mammals and Archaea for lipid biosynthesis. Since many microbes, e.g., E. coli, naturally possess a metabolic pool of acetyl-CoA, conversion of mevalonate to anhydromevalonyl-CoA can be accomplished in two enzymatic steps. We further designed and engineered a pathway that involves cloning acyl-CoA ligase (sidI) and enoyl-CoA hydratase (sidH). Finally, we engineered microbes to reduce the double bond of anhydromevalonyl-CoA to form 3-methyl-5-hydroxy-pentanoyl-CoA, catalyzed by trans-2-enoyl-CoA reductase (ter). 3-methyl-5-hydroxy-pentanoyl-CoA can spontaneously cyclize into β-methyl-δ-valerolactone.

We also have designed a hybrid approach to producing β-methyl-δ-valerolactone (FIG. 1, Route II). First, mevalonate is biosynthesized from a renewable carbon source. Then, mevalonate is converted to anhydromevalonolactone by catalytic dehydration. Anhydromevalonolactone is extracted from the reaction mixture and reduced to β-methyl-δ-valerolactone through catalytic hydrogenation. We also observed that the intermediate anhydromevalonyl-CoA could spontaneously cyclize to anhydromevalonolactone (FIG. 1, Route III), thus providing another biosynthetic/chemical hybrid route to β-methyl-δ-valerolactone.

We also have designed a non-natural pathway to produce β-methyl-δ-valerolactone (FIG. 8). Here again, we introduced a heterologous pathway into a microbial host to produce a non-native metabolite mevalonate. We again exploit the activities of sidI and sidH to generate anhydromevalonyl-coA, which can spontaneously cyclize into anhydromevalonolactone. Finally, we introduced an enoate reductase (e.g., OYE2, YqjM; Bougioukou et al., 2009, *Advanced Synthesis & Catalysis* 351:3287-3305) to reduce the double bond of anhydromevalonolactone to form β-methyl-δ-valerolactone.

Optimization of Mevalonate Production in Shake Flask

Figure 3A:
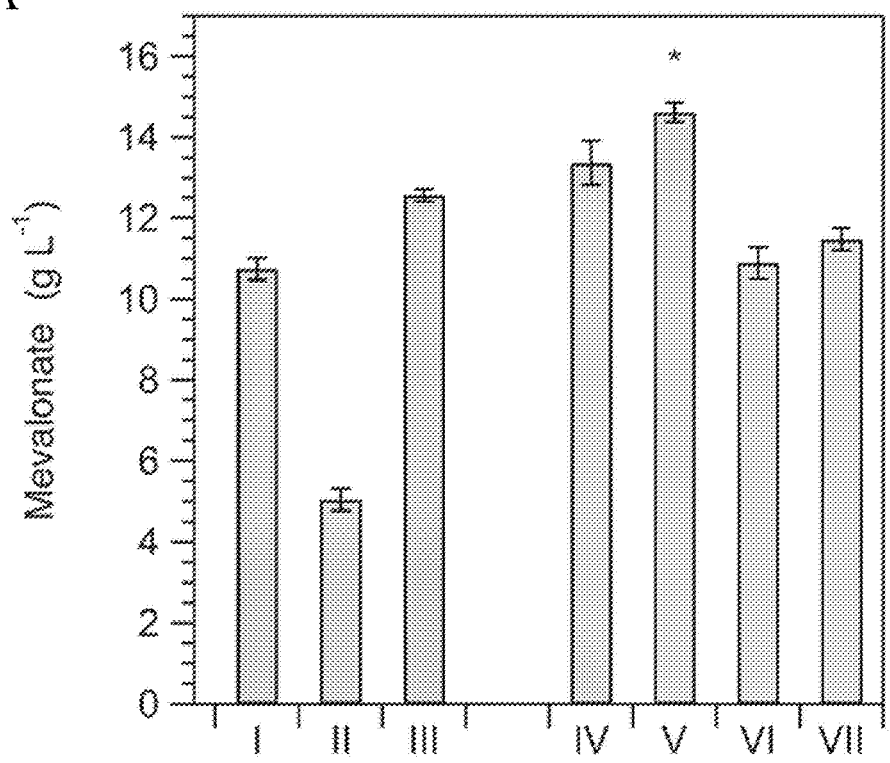
FIG. 3. Total biobased production of β-methyl-δ-valerolactone and semisynthetic route to this monomer. (A) Fermentation of mevalonate from different combinations of MvaS and MvaE. I: MvaS from E. faecalis, MvaE from E. faecalis; II: MvaS from S. aureus, MvaE from E. faecalis; III: MvaS from L. casei, MvaE from E. faecalis; IV: MvaS from L. casei, MvaE from S. aureus; V: MvaS from L. casei, MvaE from L. casei; VI: MvaS from L. casei, MvaE from M. maripaludis; VII: MvaS from L. casei, MvaE from M. voltae. (B) Anhydromevalonolactone fermentation with siderophore enzymes SidI and SidH from: A, A. fumigatus; B, N. crassa; C, P. nodorum; D, S. sclerotiorum. (C) Production of β-methyl-δ-valerolactone through fermentation with enoate-reductase: 1, Oye2 from S. cerevisiae; 2, Oye3 from S. cerevisiae; 3, wild-type YqjM from B. subtilis; 4, Mutant YqjM (C26D and I69T) from B. subtilis. (D) Production of mevalonate by fermentation of glucose in a 1.3 L bioreactor.
Figure 3B:
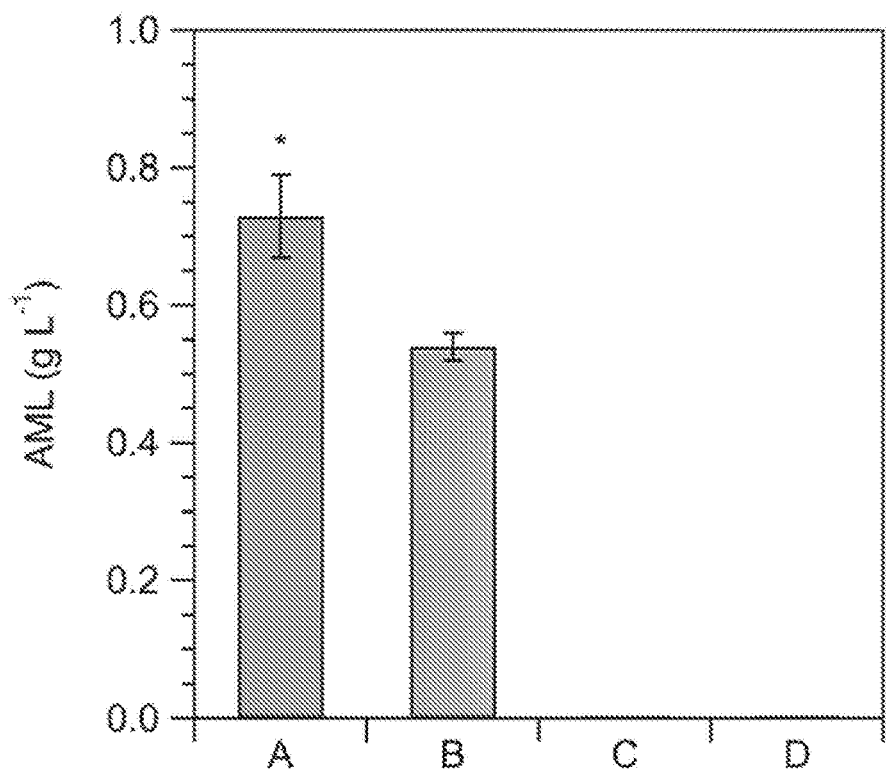
Figure 3C:
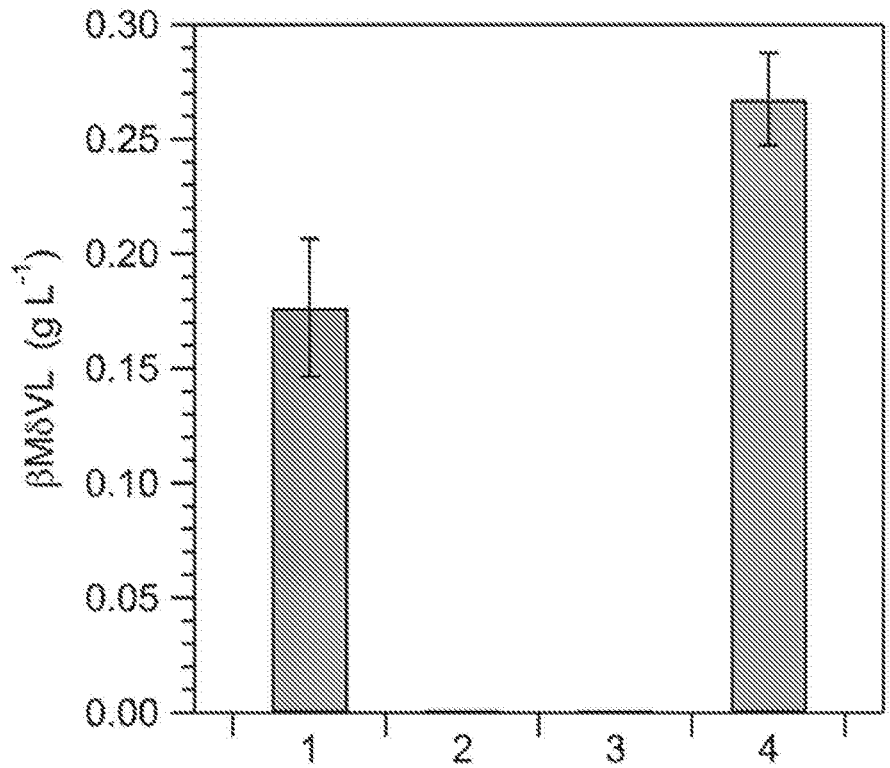

Mevalonate is the immediate metabolic precursor for our artificial biosynthetic pathway. While there was previous attempt to produce this compound in *E. coli*, the production yield and level was impractically low for industrial production. Here, we report the recombinant production of mevalonate. Specifically, we explored the effect of different combinations of HMG-CoA synthase (MvaS) and HMG-CoA reductase (MvaE). The mevalonate titer was increased 14% when using mvaS from *L. casei* instead of that from *E. faecalis* in shake flask (FIG. 3A). The strain carrying mvaS from *L. casei* was further optimized by substituting different mvaE genes. The strain with both mvaS and mvaE from *L. casei* produced 14.6 g/L mevalonate, which was 36% higher than the original strain with mvaS of *L. casei* and mvaE of *E. faecalis* (FIG. 3A). The combination with mvaS and mvaE from *L. casei* produced 50% more mevalonate than a previously reported construct with possessing mvaS and mvaE from *E. faecalis*. (Tabata et al. 2004, *Biotechnol Lett* 26:1487-1491).

Mevalonate Production in 1.3 L Bioreactor

Figure 3D:
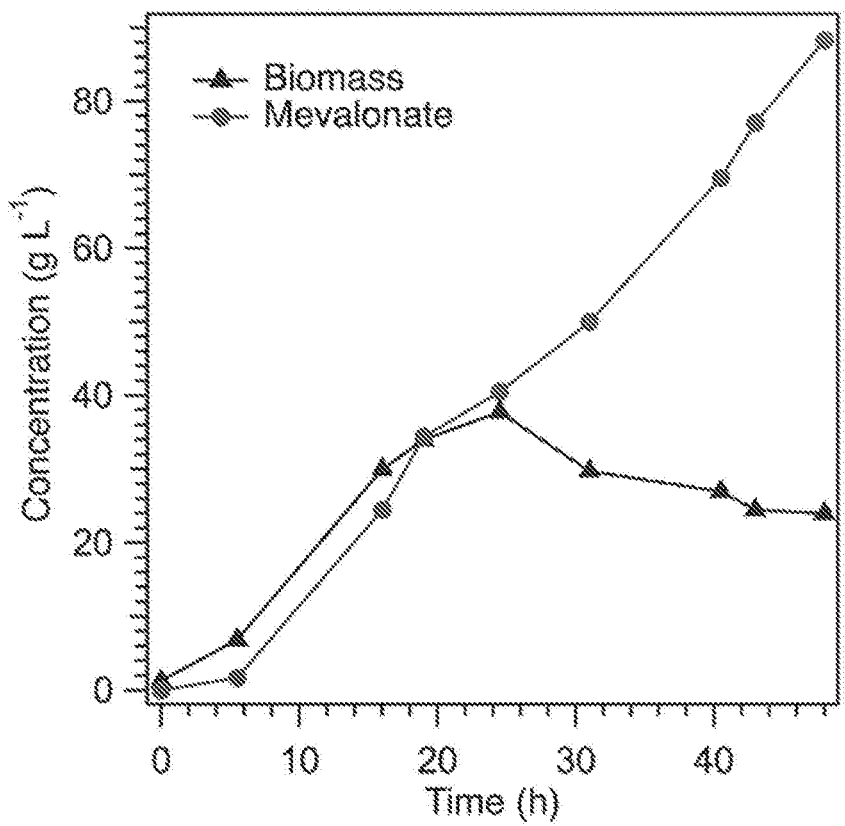
Figure 4:
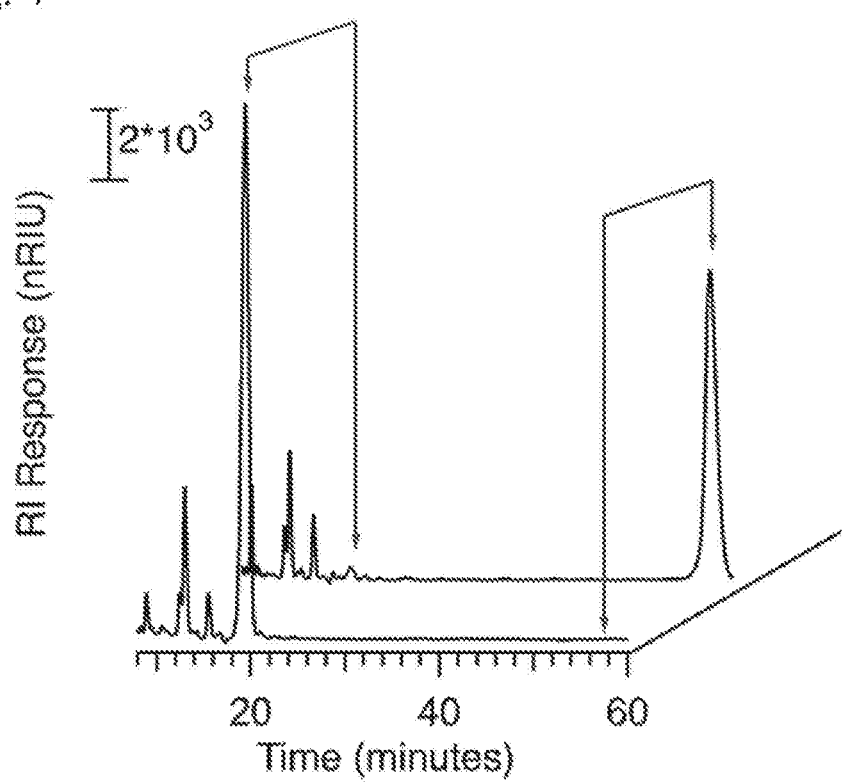
FIG. 4. Acid catalyzed dehydration of mevalonate to anhydromevalonolactone monitored by refractive index (RI).

The strain carrying mvaS and mvaE from *L. casei* was chosen to perform scale-up fermentation in a 1.3 L bioreactor. The biomass increased to 38 g/L after 24 hours, and then decreased gradually during fermentation (FIG. 3D). Acetate accumulated to 2.3 g/L in the first six hours due to fast growth rate, then decreased and maintained at a very low level until 32 hours. As the concentration of mevalonate reached 51 g/L, the glucose consumption rate decreased and acetate increased gradually. When acetate reached 3.5 g/L after 48 hours, fermentation was stopped. The mevalonate productivity was around 2 $gL^{-1}$ $h^{-1}$ throughout the whole fermentation process. The final titer of mevalonate after 48 hours was 88.3 g/L, and the yield from glucose is around 0.26 g/g. The mevalonate titer was increase 87.9% compared to the previous report. (Tabata et al. 2004, *Biotechnol Lett* 26:1487-1491).

After introducing the second plasmid pZAlac-sidI-sidH-ter into the mevalonate-producing *E. coli*, we detected about 20 mg/L anhydromevalonolactone, but β-methyl-δ-valerolactone or its hydrolyzed acid form was not found in the fermentation broth.

Catalytic Dehydration and Extraction

Though anhydromevalonolactone can be converted into β-methyl-δ-valerolactone by catalytic hydrogenation, its fermentation concentration was still too low for industrial application. Thus, we developed an alternative approach by chemically converting mevalonate into β-methyl-δ-valerolactone (Route II, FIG. 1). Sulfuric acid was chosen as the catalyst to enable dehydration reaction. 5 mL fermentation samples with an addition of 0.1 to 0.6 mL sulfuric acid were placed in 15 mL test tubes. The reaction was performed in an autoclave for one hour (121° C., 15 psi). Almost all the mevalonate was converted into anhydromevalonolactone when 5 mL $H_2SO_4$ was used (FIGS. 5A and 5B), which suggested that acid was a selective catalyst to dehydrate the tertiary alcohol group.

Figure 6:
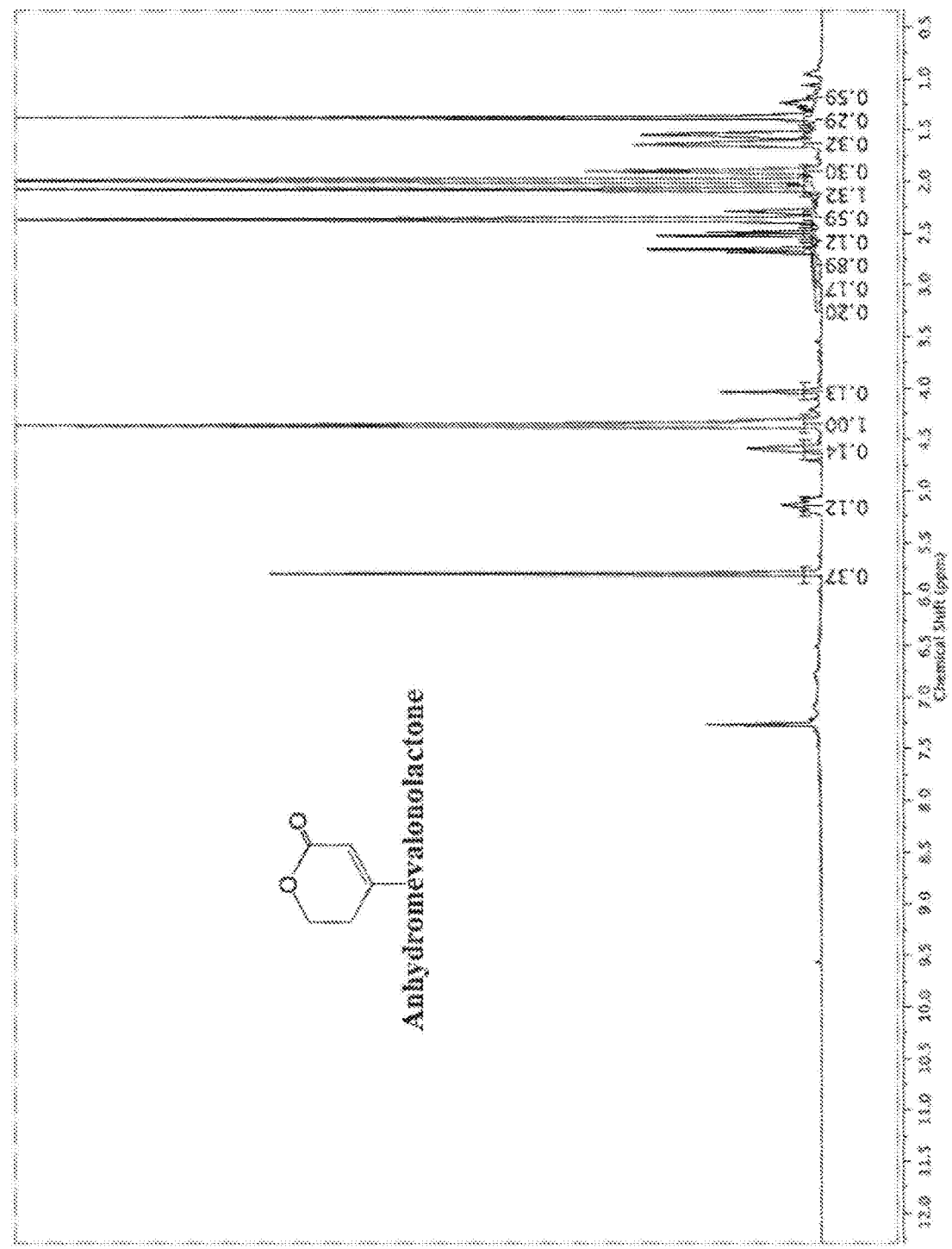
FIG. 6. NMR spectrum the extracted anhydromevalonolactone.

Purification of anhydromevalonolactone also was studied by extraction with different organic solvents (Table 1). Approximately 96% of the anhydromevalonolactone was extracted when chloroform was applied at a 1:1 volume ratio. The partition coefficient Kd for anhydromevalonolactone in between chloroform and water was 25. NMR analysis indicated the anhydromevalonolactone was in the lactone form, instead of equilibrating with its hydroxyacid form (FIG. 6).

TABLE 1

The extract efficiency and Kd of different solvents

| Solvents | Anhydromevalonolactone extract efficiency (%) | Kd |
|---|---|---|
| MIBK | 79.90 | 3.97 |
| DIBK | 44.15 | 0.79 |
| Oley | 35.56 | 0.55 |
| ethyl acetate | 79.67 | 3.92 |
| CHCl3 | 96.14 | 24.89 |
| Benzene | 65.26 | 1.88 |

Hydrogenation

Figure 7:
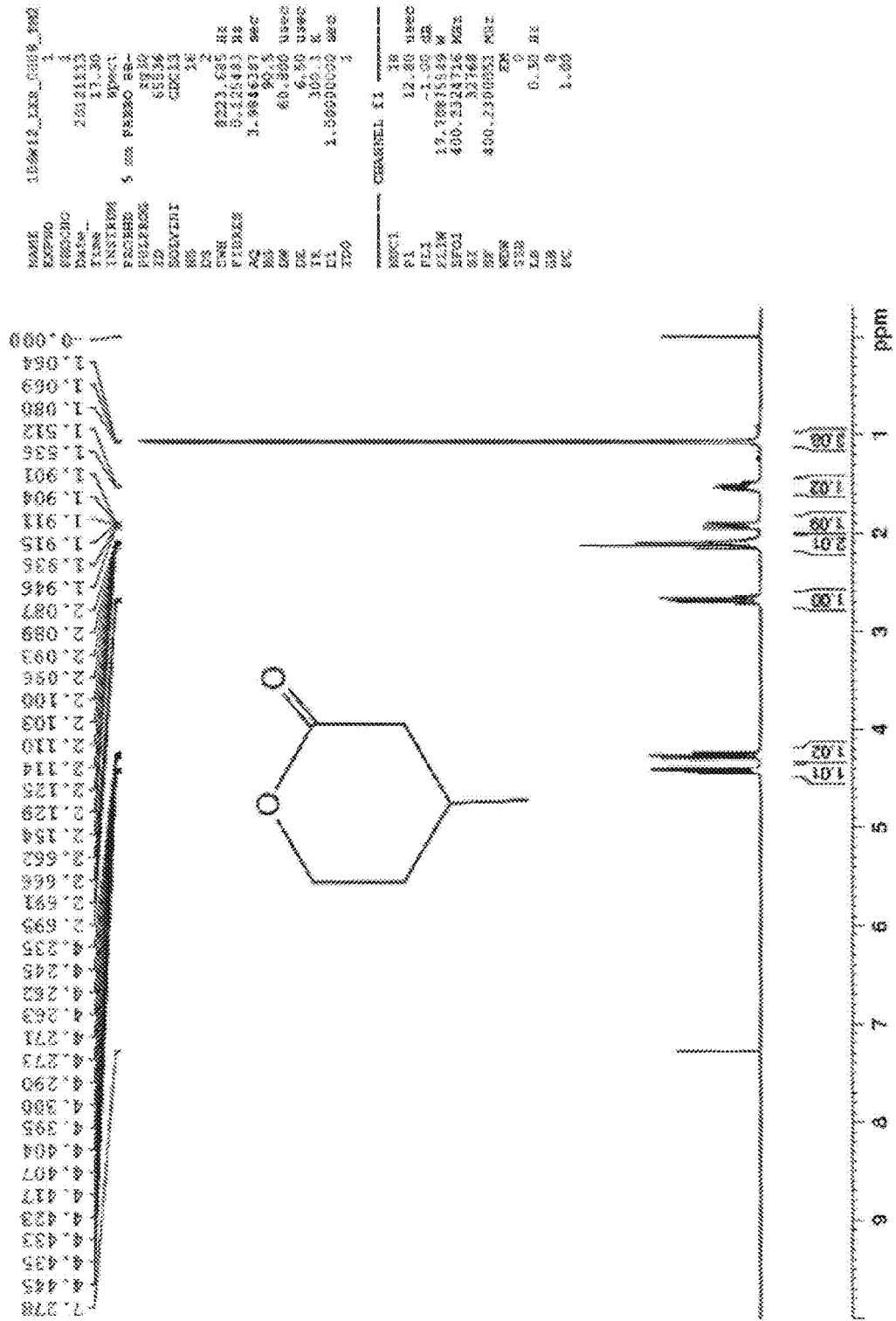
FIG. 7. NMR spectrum hydrogenated sample of anhydromevalonolactone.

Anhydromevalonolactone (5.7 g) was dissolved in 700 mL methanol. Catalyst Pd/C (2 g) was added. The pressure of $H_2$ was maintained at 4 bar. After reaction at 25° C. overnight (~14 hours), the product was column purified and the oily β-methyl-δ-valerolactone was obtained with a yield of 87.93% (FIG. 7).

Alternative Biosynthesis of Anhydromevalonolactone and Mevalonolactone

Alternative pathways to producing anhydromevalonolactone involve further modifying a microbe to include sidI and sidH from *Aspergillus fumigatus*, *Neurospora crassa*, *Phaeosphaeria nodorum*, or *Sclerotinia sclerotiorum*. Table 2 shows anhydromevalonolactone fermentation results when the sidI-sidH-containing plasmids were introduced into mevalonate-producing *E. coli*. The strain carrying sidI and sidH from *Aspergillus fumigatus* produced 730 mg/L anhydromevalonolactone; the strain carrying sidI and sidH from *Neurospora crassa* produced 540 mg/L anhydromevalonolactone.

TABLE 2

The anhydromevalonolactone fermentation results (g/L)

| Strain | Mevalonate | Anhydromevalonolactone |
|---|---|---|
| BW25113 with pMEV-7 and pAML-1 | 12.36 ± 1.18 | 0.73 ± 0.06 |
| BW25113 with pMEV-7 and pAML-2 | 13.59 ± 0.24 | 0.54 ± 0.02 |

Enoate reductases such as, for example, OYE2 and OYE3 from *S. cerevisiae* or yqjM from *B. subtilis* can catalyze reactions using 3-methylcyclohexenone and/or 3-methylcyclohexanone as a native substrate. We introduced coding regions for OYE2, OYE3, wild type yqjM, or a mutant yqjM into an anhydromevalonolactone-producing microbe to determine whether each construct could synthesize the final monomer of mevalonolactone. Results are shown in Table 3.

TABLE 3

The βMδVL fermentation results (g/L)

| Strain | Mevalonate | Anhydromevalonolactone | βMδVL |
|---|---|---|---|
| BW25113 with pMEV-7 and pMVL-1 | 10.19 ± 0.61 | 0.34 ± 0.03 | 0.18 ± 0.03 |
| BW25113 with pMEV-7 and pMVL-2 | 6.77 ± 0.58 | 0.48 ± 0.03 | 0 |
| BW25113 with pMEV-7 and pMVL-3 | 8.85 ± 0.56 | 0.55 ± 0.01 | 0 |
| BW25113 with pMEV-7 and pMVL-4 | 9.39 ± 0.48 | 0.31 ± 0.01 | 0.27 ± 0.02 |

Thus, in one aspect, this disclosure describes biosynthesized compounds, recombinant microbes that produce the biosynthesized compounds, and methods of producing the biosynthesized compounds. As used herein, a "biosynthesized compound" is a compound in which at least one step of its synthesis is performed by a microbe. In some cases, the biosynthesized compound may be β-methyl-δ-valerolactone. As illustrated in FIG. 1 and FIG. 8, there are multiple routes by which a biosynthesized β-methyl-δ-valerolactone compound may be produced. Route I involves biosynthesis of β-methyl-δ-valerolactone by a microbe from a carbon source in a culture medium. Route II and Route III illustrated in FIG. 1 show that an intermediate compound (e.g., biosynthesized anhydromevalonolactone) may be harvested and subjected to one or more chemical steps to produce biosynthesized β-methyl-δ-valerolactone. The pathway illustrated in FIG. 8 involves an alternative fully biosynthetic route to β-methyl-δ-valerolactone.

One can distinguish a biosynthesized compound as described herein from a similar compound produced by conventional chemical processes from, for example, a petroleum-based material by the ratio of $^{14}C$ to $^{12}C$ in a sample of the compound. A sample of the compound that is biosynthesized will possess a measurable amount of $^{14}C$ isotopes incorporated into the compound molecules, while a sample of the compound prepared from petroleum-based materials will possess negligible levels of $^{14}C$. Thus, a sample or composition that includes a biosynthesized compound (e.g., either β-methyl-δ-valerolactone or anhydromevalonolactone) will possess a $^{14}C/^{12}C$ ratio greater than zero. In some cases, a sample or composition that includes a biosynthesized compound can have a $^{14}C/^{12}C$ ratio greater than $0.25 \times 10^{-12}$ such as, for example, a $^{14}C/^{12}C$ ratio from $0.25 \times 10^{-12}$ to $1.2 \times 10^{-12}$.

A biosynthesized compound as described herein, whether β-methyl-δ-valerolactone and/or anhydromevalonolactone, is produced by a method, described in more detail below, in which a host cell is modified to be a recombinant cell that can exhibit increase biosynthesis of the biosynthetic compound compared to a wild-type control. In some cases, the wild-type control may be unable to produce the biosynthetic compound and, therefore, an increase in the biosynthesis of the biosynthetic compound may reflect any measurable biosynthesis of that compound. In certain embodiments, an increase in the biosynthesis of a biosynthetic compound can include biosynthesis sufficient for a culture of the microbial cell to accumulate the biosynthetic compound to a predetermine concentration.

The predetermined concentration may be any predetermined concentration of the biosynthetic compound suitable for a given application. Thus, a predetermined concentration may be, for example, a concentration of at least 0.1 g/L such as, for example, at least 0.25 g/L, at least 0.5 g/L, at least 1.0 g/L, at least 2.0 g/L, at least 3.0 g/L, at least 4.0 g/L, at least 5.0 g/L, at least 6.0 g/L, at least 7.0 g/L, at least 8.0 g/L, at least 9.0 g/L, at least 10 g/L, at least 20 g/L, at least 50 g/L, at least 100 g/L, or at least 200 g/L.

Thus, in another aspect, this disclosure describes methods of making biosynthesized compounds including, for example, β-methyl-δ-valerolactone and/or anhydromevalonolactone. FIG. 1 illustrates three different exemplary biosynthetic routes to producing β-methyl-δ-valerolactone. FIG. 8 illustrates an alternative exemplary biosynthetic routes to producing β-methyl-δ-valerolactone.

One method, illustrated as Route I in FIG. 1, involves biosynthesis by a recombinant cell of 3-methyl-5-hydroxypentanoyl-CoA, which spontaneously converts to β-methyl-δ-valerolactone. Thus, in some embodiments, the method includes culturing an appropriate recombinant cell—described in more detail below—under conditions effective for the recombinant cell to exhibit increased biosynthesis of 3-methyl-5-hydroxypentanoyl-CoA compared to a wild-type control, then allowing the 3-methyl-5-hydroxypentanoyl-CoA to spontaneously convert to β-methyl-δ-valerolactone.

In alternative embodiments, the methods can include a combined biosynthetic-chemical approach. In some of these embodiments, reflected in Route III in FIG. 1, a recombinant cell modified to exhibit increased biosynthesis of anhydromevalonyl-CoA compared to a wild-type control can be grown in culture under conditions effective for the recombinant cell to produce anhydromevalonyl-CoA. The anhydromevalonyl-CoA may be harvested and allowed to spontaneously convert to anhydromevalonolactone. The anhydromevalonolactone may be converted to β-methyl-δ-valerolactone via one or more chemical steps described in more detail below.

In another combined biosynthetic-chemical approach, reflected as Route II in FIG. 1, a recombinant cell modified to exhibit increased biosynthesis of mevalonate (or its lactone form mevalonolactone) compared to a wild-type control can be grown in culture under conditions effective for the recombinant cell to produce mevalonate (or mevalonolactone). The mevalonate (or mevalonolactone) may be harvested and converted to anhydromevalonolactone. The anhydromevalonolactone may be converted to β-methyl-δ-valerolactone via one or more chemical steps described in more detail below.

In still other embodiments, the method can involve biosynthesis of anhydromevalonyl-CoA, which can spontaneously convert to anhydromevalonolactone, which can, in turn, be enzymatically converted to β-methyl-δ-valerolactone. Thus, in some embodiments, the method includes culturing an appropriate recombinant cell—described in more detail below—under conditions effective for the recombinant cell to exhibit increased biosynthesis of anhydromevalonyl-CoA and increased conversion of anhydromevalonolactone to β-methyl-δ-valerolactone.

In some embodiments, the conversion of mevalonate (or mevalonolactone) to anhydromevalonolactone can include dehydrating the mevalonate (or mevalonolactone) using a dehydration catalyst under appropriate conditions for the dehydration catalyst to dehydrate the mevalonate (or mevalonolactone) to anhydromevalonolactone. Exemplary dehydration catalysts can include, for example, tosylic acid, sulfuric acid and phosphoric acid, or solid acid catalysts such as zeolites, Amberlyst 70 and Amberlyst 15. In some embodiments, the dehydration catalyst may be provided in a catalytic amount of at least 0.1 equivalents relative to mevalonate (or mevalonolactone). In some of these embodiments, the dehydration catalyst may be provided in a catalytic amount of no more than 20.0 equivalents relative to mevalonate (or mevalonolactone). In some embodiments, the dehydration may be performed at a temperature of no less than room temperature such as for example, at least 20° C., at least 30° C., at least 40° C., at least 50° C., at least 60° C., at least 70° C., at least 80° C., at least 90° C., or at least 100° C.

The recombinant cell modified to exhibit increased biosynthesis of mevalonate (or its lactone form mevalonolactone) compared to a wild-type control can be any suitable recombinant cell. While exemplary embodiments described herein include a genetically modified *E. coli* host cell, the recombinant cells described herein can be constructed, and the methods of making and using the recombinant cells can be performed, using any suitable host cell. Thus, the recombinant cell can be, or be derived from, any suitable microbe including, for example, a prokaryotic microbe or a eukaryotic microbe. As used herein, the term "or derived from" in connection with a microbe simply allows for the "host cell" to possess one or more genetic modifications before being modified to exhibit the indicated increased biosynthetic activity. Thus, the term "recombinant cell" encompasses a "host cell" that may contain nucleic acid material from more than one species before being modified to exhibit the indicated biosynthetic activity.

In some embodiments, the host cell may be selected to possess one or more natural physiological activities. For example, the host cell may be photosynthetic (e.g., cyanobacteria) or may be cellulolytic (e.g., *Clostridium cellulolyticum*).

In some embodiments, the recombinant cell may be, or be derived from, a eukaryotic microbe such as, for example, a fungal cell. In some of these embodiments, the fungal cell may be, or be derived from, a member of the Saccharomycetaceae family such as, for example, *Saccharomyces cerevisiae, Candida rugosa,* or *Candida albicans*. In some of these embodiments, yield can be improved by at least partially knocking out activity of the host cell's native mevalonate consuming pathways.

In other embodiments, the recombinant cell may be, or be derived from, a prokaryotic microbe such as, for example, a bacterium. In some of these embodiments, the bacterium may be a member of the phylum Protobacteria. Exemplary members of the phylum Protobacteria include, for example, members of the Enterobacteriaceae family (e.g., *Escherichia coli*) and, for example, members of the Pseudomonaceae family (e.g., *Pseudomonas putida*). In other cases, the bacterium may be a member of the phylum Firmicutes. Exemplary members of the phylum Firmicutes include, for example, members of the Bacillaceae family (e.g., *Bacillus subtilis*), members of the Clostridiaceae family (e.g., *Clostridium cellulolyticum*) and, for example, members of the Streptococcaceae family (e.g., *Lactococcus lactis*). In other cases, the bacterium may be a member of the phylum Cyanobacteria. Here again, in some of these embodiments, yield can be improved by at least partially knocking out activity of the host cell's native mevalonate consuming pathways.

In some embodiments, the recombinant cell can exhibit increased activity compared to a wild-type control of one or more enzymes involved in a metabolic biosynthetic pathway for producing mevalonate (or mevalonolactone). As used herein, the terms "activity" with regard to particular enzyme refers to the ability of a polypeptide, regardless of its common name or native function, to catalyze the conversion of the enzyme's substrate to a product, regardless of whether the "activity" as less than, equal to, or greater than the native activity of the identified enzyme. Methods for measuring the biosynthetic activities of cells are routine and well known to those of ordinary skill in the art.

As used herein, an increase in catalytic activity can be quantitatively measured and described as a percentage of the catalytic activity of an appropriate wild-type control. The catalytic activity exhibited by a genetically-modified polypeptide can be, for example, at least 110%, at least 125%, at least 150%, at least 175%, at least 200% (two-fold), at least 250%, at least 300% (three-fold), at least 400% (four-fold), at least 500% (five-fold), at least 600% (six-fold), at least 700% (seven-fold), at least 800% (eight-fold), at least 900% (nine-fold), at least 1000% (10-fold), at least 2000% (20-fold), at least 3000% (30-fold), at least 4000% (40-fold), at least 5000% (50-fold), at least 6000% (60-fold), at least 7000% (70-fold), at least 8000% (80-fold), at least 9000% (90-fold), at least 10,000% (100-fold), or at least 100,000% (1000-fold) of the activity of an appropriate wild-type control.

Alternatively, an increase in catalytic activity may be expressed as at an increase in $k_{cat}$ such as, for example, at least a two-fold increase, at least a three-fold increase, at least a four-fold increase, at least a five-fold increase, at least a six-fold increase, at least a seven-fold increase, at least an eight-fold increase, at least a nine-fold increase, at least a 10-fold increase, at least a 15-fold increase, or at least a 20-fold increase in the $k_{cat}$ value of the enzymatic conversion.

An increase in catalytic activity also may be expressed in terms of a decrease in $K_m$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $K_m$ value of the enzymatic conversion.

A decrease in catalytic activity can be quantitatively measured and described as a percentage of the catalytic activity of an appropriate wild-type control. The catalytic activity exhibited by a genetically-modified polypeptide can be, for example, no more than 95%, no more than 90%, no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, no more than 5%, no more than 4%, no more than 3%, no more than 2%, no more than 1% of the activity, or 0% of the activity of a suitable wild-type control.

Alternatively, a decrease in catalytic activity can be expressed as an appropriate change in a catalytic constant. For example, a decrease in catalytic activity may be expressed as at a decrease in $k_{cat}$ such as, for example, at least a two-fold decrease, at least a three-fold decrease, at least a four-fold decrease, at least a five-fold decrease, at least a six-fold decrease, at least a seven-fold decrease, at least an eight-fold decrease, at least a nine-fold decrease, at least a 10-fold decrease, at least a 15-fold decrease, or at least a 20-fold decrease in the $k_{cat}$ value of the enzymatic conversion.

A decrease in catalytic activity also may be expressed in terms of an increase in $K_m$ such as, for example, an increase in $K_m$ of at least two-fold, at least three-fold, at least four-fold, at least five-fold, at least six-fold, at least seven-fold, at least an eight-fold, at least nine-fold, at least 10-fold, at least 15-fold, at least 20-fold, at least 25-fold, at least 30-fold, at least 35-fold, at least 40-fold, at least 45-fold, at least 50-fold, at least 75-fold, at least 100-fold, at least 150-fold, at least 200-fold, at least 230-fold, at least 250-fold, at least 300-fold, at least 350-fold, or at least 400-fold.

Exemplary enzymes that may be part of such an engineered biosynthetic pathway include, for example, a thiolase, 3-hydroxy-3-methyl-glutaryl (HMG)-CoA synthase, and HMG-CoA reductase. The thiolase may be any suitable thiolase that is natively expressed by any organism. In some embodiments, the thiolase can include AtoB such as, for example, the enzyme encoded by a polynucleotide that includes the atoB coding region isolated from *E. coli*. The HMG-CoA synthase may be any suitable HMG-CoA synthase that is natively expressed by any organism. In some embodiments, the HMG-CoA synthase can include MvaS such as, for example, an enzyme encoded by a polynucleotide that includes a myaS coding region isolated from a member of the genus *Enterococcus*, a member of the genus *Staphylococcus*, a member of the genus *Lactobacillus*, or a member of the genus *Methanococcus*. The HMG-CoA reductase may be any suitable HMG-CoA reductase that is natively expressed by any organism. In some embodiments, the HMG-CoA reductase can include MvaE such as, for example, an enzyme encoded by a polynucleotide that includes a myaE coding region isolated from a member of the genus *Enterococcus*, a member of the genus *Staphylococcus*, a member of the genus *Lactobacillus*, or a member of the genus *Methanococcus*.

In some embodiments, the method may be performed by growing the recombinant cells in a cell culture that includes medium that has, as a carbon source, one or more of glucose, glycerol, xylose, arabinose, glucaric acid, galactaric acid, galacturonic acid, alginate, starch, sucrose, or cellulose.

Regardless of whether one follows Route II, Route III, or some other metabolic route to anhydromevalonolactone, the anhydromevalonolactone may be converted to β-methyl-δ-valerolactone by catalytic hydrogenation of the anhydromevalonolactone. In some embodiments, the anhydromevalonolactone may be hydrogenated in an organic solvent in the presence of a heterogeneous catalyst or homogenous catalyst. Exemplary heterogeneous catalysts include, for example, palladium on activated carbon, nickel on silica, and nickel on alumina. Exemplary homogenous catalysts include, for example, $NaBH_4$, $LiAlH_4$, sulfuric acid, phosphoric acid, and mevalonic acid. The catalytic hydrogenation of anhydromevalonolactone may be performed under any appropriate set of conditions. For example, the catalytic hydrogenation of anhydromevalonolactone may be performed at a temperature of no more than 100° C. and/or at a hydrogen pressure of no more than 100 bar.

β-methyl-δ-valerolactone so produced may be collected by any suitable method including, for example, distilling the β-methyl-δ-valerolactone such as, for example, by using a staged distillation column at a pressure of no more than 1 atm.

In some embodiments, one can obtain β-methyl-δ-valerolactone with a recovery rate of at least 70% such as, for example, at least 75%, at least 80%, at least 85%, or at least 90%.

In some embodiments, the method can include a step of extracting the anhydromevalonolactone prior to the catalytic dehydrogenation. Such a step can increase the efficiency of the catalytic dehydrogenation of anhydromevalonolactone and, therefore, increase the final yield of β-methyl-δ-valerolactone. In some embodiments, the extraction may be performed using a water-immiscible extractant such as, for example, an amide, an ether, a ketone, an alkane, an alcohol, an ester, benzene, xylene, chloroform, or any combination of two or more water-immiscible extractants. In some of these embodiments, the extraction can recover at least 70% of the anhydromevalonolactone such as, for example, at least 75%, at least 80%, at least 85%, or at least 90% of the anhydromevalonolactone. Even with a recovery of less than 100% of the anhydromevalonolactone, the increased concentration of anhydromevalonolactone that results from an extraction step can improve the ultimate yield of β-methyl-δ-valerolactone.

In some embodiments, anhydromevalonolactone may be biosynthetically converted to β-methyl-δ-valerolactone. Exemplary enzymes that may catalyze the biosynthetic conversion of anhydromevalonolactone to β-methyl-δ-valerolactone includes, for example, an enoate reductase. In some embodiments, the enoate reductase can include, for example, OYE2 or OYE3 such as, for example, an enzyme encoded by a polynucleotide that includes an oye2 or oye3 coding region isolated from a member of the Saccharomycetaceae family such as, for example, *Saccharomyces cerevisiae*. In other embodiments, the enoate reductase can include, for example, YqjM such as, for example, an enzyme encoded by a polynucleotide a yqjM coding region isolated from a member of the Bacillaceae family such as, for example, *Bacillus subtilis*.

A recombinant cell useful for biosynthesis of mevalonate is described above. As described above, such a recombinant cell may be used to produce a biosynthetic compound as described herein—e.g., anhydromevalonolactone and/or β-methyl-δ-valerolactone—via Route II illustrated in FIG. 1. Alternatively, a recombinant cell useful for biosynthesis of mevalonate (or mevalonolactone) may be further modified to biosynthesize anhydromevalonolactone (anhydromevalonate) and/or β-methyl-δ-valerolactone via Route I or Route III illustrated in FIG. 1. Thus, in another aspect, this disclosure describes recombinant cells useful for biosynthesis according to Route I or Route III as illustrated in FIG. 1.

In some embodiments, the recombinant cell can be modified to exhibit increased biosynthesis of anhydromevalonyl-CoA compared to a wild-type control. Such a recombinant cell can exhibit increased activity, compared to a wild-type control, of a thiolase, a HMG-CoA synthase, and/or a HMG-CoA reductase, as described above with respect to recombinant cells useful for biosynthesis of mevalonate (or mevalonolactone). In addition, a recombinant cell useful for biosynthesis of anhydromevalonyl-CoA and/or anhydromevalonolactone (or anhydromevalonate) can be modified to exhibit increased activity compared to a wild-type control of an acyl-CoA ligase and/or an enoyl-CoA hydratase.

The acyl-CoA ligase may be any suitable acyl-CoA ligase that is natively expressed by any organism. In some embodiments, the acyl-CoA ligase can include SidI such as, for example, the enzyme encoded by a polynucleotide that includes the sidI coding region isolated from a microorganism that produces a siderophore that comprises an anhydromevalonyl unit. Thus, suitable exemplary acyl-CoA ligases can include an acyl-CoA ligase encoded by the coding region of a polynucleotide isolated from a member of the genus *Aspergillus* such as, for example, *Aspergillus fumigatus*. Similarly, the enoyl-CoA hydratase may be any suitable enoyl-CoA hydratase that is natively expressed by any organism. In some embodiments, the enoyl-CoA hydratase can include SidH such as, for example, the enzyme encoded by a polynucleotide that includes the sidH coding region isolated from a microorganism that produces a siderophore that comprises an anhydromevalonyl unit. Thus, suitable exemplary enoyl-CoA hydratases can include an enoyl-CoA hydratase encoded by the coding region of a polynucleotide isolated from a member of the genus *Aspergillus* such as, for example, *Aspergillus fumigatus*.

In some embodiments, the recombinant cell may be still further modified to exhibit increased biosynthesis of 3-methyl-5-hydroxypentanoyl-CoA compared to a wild-type control. In some embodiments, such a recombinant cell can exhibit an increased ability to accumulate β-methyl-δ-valerolactone in culture compared to a wild-type control. In such embodiments, the recombinant cell can be modified to exhibits increased activity, compared to a wild-type control, of a thiolase, a HMG)-CoA synthase, a HMG-CoA reductase, an acyl-CoA ligase, and/or an enoyl-CoA hydratase as described above. In addition, a recombinant cell useful for biosynthesis of 3-methyl-5-hydroxypentanoyl-CoA—which spontaneously converts to β-methyl-δ-valerolactone—can be modified to exhibit increased activity compared to a wild-type control of an enoyl-Coa reductase activity. The enoyl-CoA reductase may be any suitable enoyl-CoA that is natively expressed by any organism. In some embodiments, the enoyl-CoA reductase can include Ter such as, for example, the enzyme encoded by a polynucleotide that includes the ter coding region isolated from *T. denticola*.

In constructing the various recombinant cells described herein, a heterologous polynucleotide encoding a heterologous polypeptide may be inserted into a vector. As used herein, a vector is a replicating polynucleotide such as, for example, a plasmid, phage, or cosmid, to which another polynucleotide may be inserted so as to bring about the replication of the inserted polynucleotide. Construction of vectors containing a polynucleotide of the invention employs standard ligation techniques known in the art. See, e.g., Sambrook et al, *Molecular Cloning: A Laboratory Manual.*, Cold Spring Harbor Laboratory Press (1989). A vector can permit, for example, further cloning—i.e., a cloning vector—or expression of the polypeptide encoded by the coding region—i.e., an expression vector. The term vector includes, but is not limited to, plasmid vectors, viral vectors, cosmid vectors, or artificial chromosome vectors. In one embodiment, the vector is a plasmid. Selection of a vector can depend upon a variety of desired characteristics in the resulting construct, such as a selection marker, vector replication rate, and the like.

An expression vector optionally includes regulatory sequences operably linked to the coding region. The polynucleotides described herein are not limited by the use of any particular promoter, and a wide variety of promoters are known. Promoters act as regulatory signals that bind RNA polymerase in a cell to initiate transcription of a downstream (3' direction) coding region. The promoter used can be a constitutive or an inducible promoter. It can be, but need not be, heterologous with respect to the host cell. Exemplary promoters include, for example, trp, tac, and T7.

"Coding sequence" or "coding region" refers to a nucleotide sequence that encodes a polypeptide and, when placed under the control of appropriate regulatory sequences, expresses the encoded polypeptide. The boundaries of a coding region are generally determined by a translation start codon at its 5' end and a translation stop codon at its 3' end. As used herein, the term "polypeptide" refers broadly to a polymer of two or more amino acids joined together by peptide bonds. The term "polypeptide" also includes molecules that contain more than one polypeptide joined by disulfide bonds, ionic bonds, or hydrophobic interactions, or complexes of polypeptides that are joined together, covalently or noncovalently, as multimers (e.g., dimers, tetramers). Thus, the terms peptide, oligopeptide, and protein are all included within the definition of polypeptide and these terms are used interchangeably. The term "polypeptide" does not connote a specific length of a polymer of amino acids, nor does it imply or distinguish whether the polypeptide is produced using recombinant techniques, chemical or enzymatic synthesis, or is naturally occurring.

"Regulatory sequence" refers to a nucleotide sequence that regulates expression of a coding region to which it is operably linked. Nonlimiting examples of regulatory sequences include, for example, promoters, transcription initiation sites, translation start sites, translation stop sites, and terminators. "Operably linked" refers to a juxtaposition wherein the components are in a relationship permitting them to function in their intended manner. A regulatory sequence is "operably linked" to a coding region when it is joined in such a way that expression of the coding region is achieved under conditions compatible with the regulatory sequence.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Bacterial and Growth Conditions

BW25113 (rrnB$_{T14}$ ΔlacZ$_{WJ16}$ hsdR514 ΔaraBAD$_{AH33}$ ΔrhaBAD$_{LD78}$) was used to produce (R)-mevalonate and βMδVL. (Datsenko et al., 2000, *Proc Natl Acad Sci USA* 97:6640-6645) All cloning procedures were carried out in the *E. coli* strain XL10-gold (Stratagene, Agilent Technologies, Inc., Santa Clara, Calif.). These *E. coli* strains were grown in test tubes at 37° C. in 2× YT rich medium (16 g/L Bacto-tryptone, 10 g/L yeast extract and 5 g/L NaCl) supplemented with appropriate antibiotics (ampicillin 100 μg/mL and kanamycin 50 μg/mL) unless otherwise specified.

Plasmid Construction

Figure 2:
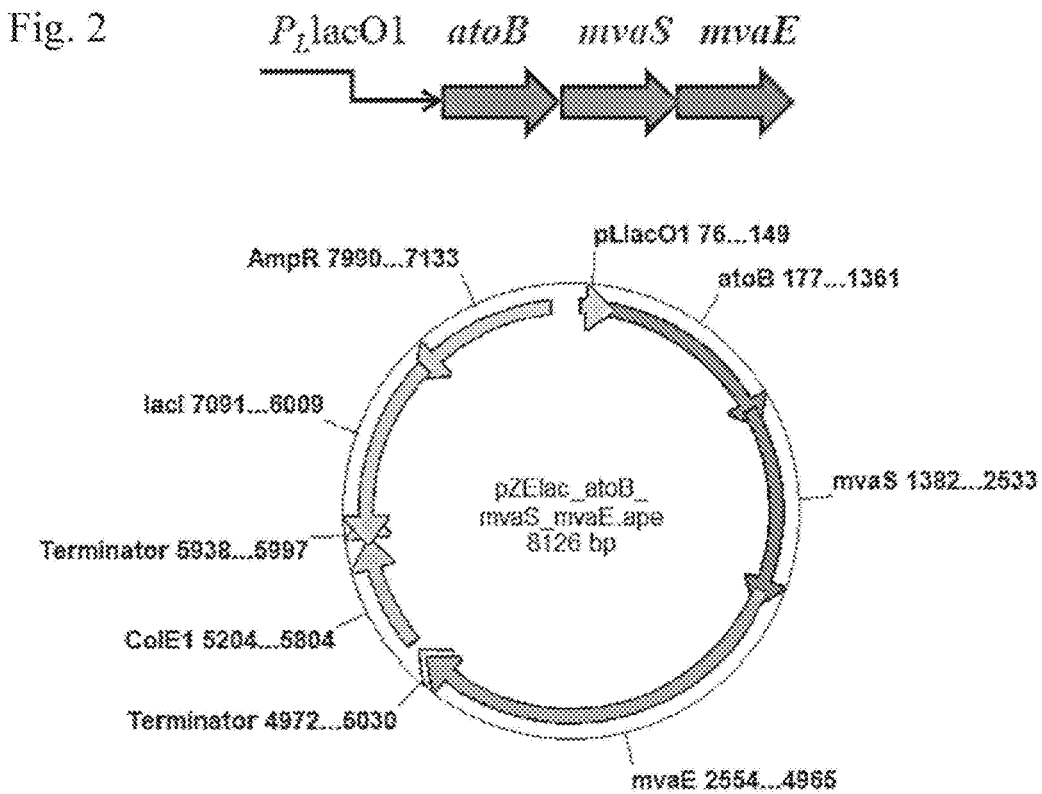
FIG. 2. Plasmids constructed for testing βMδVL production.
Figure 2:
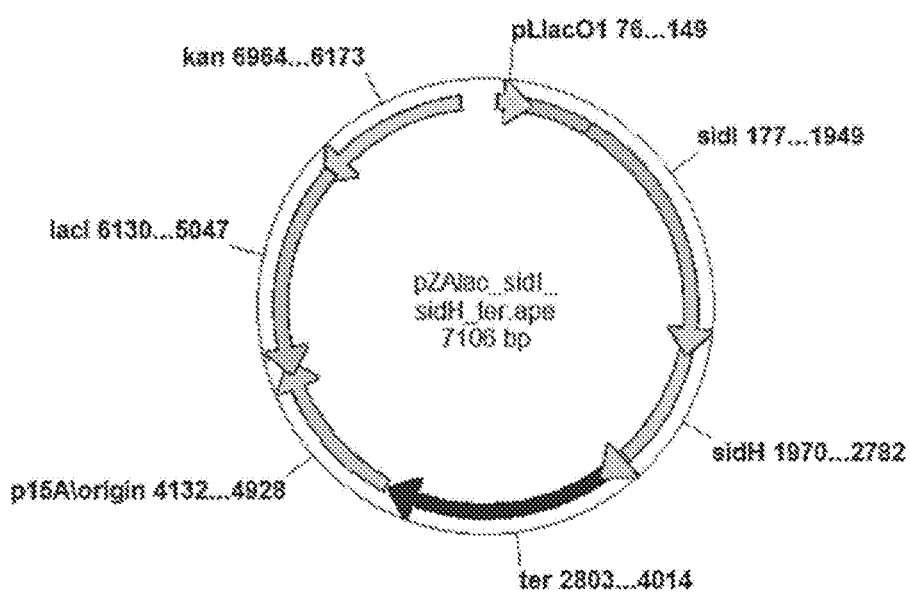
Figure 9:
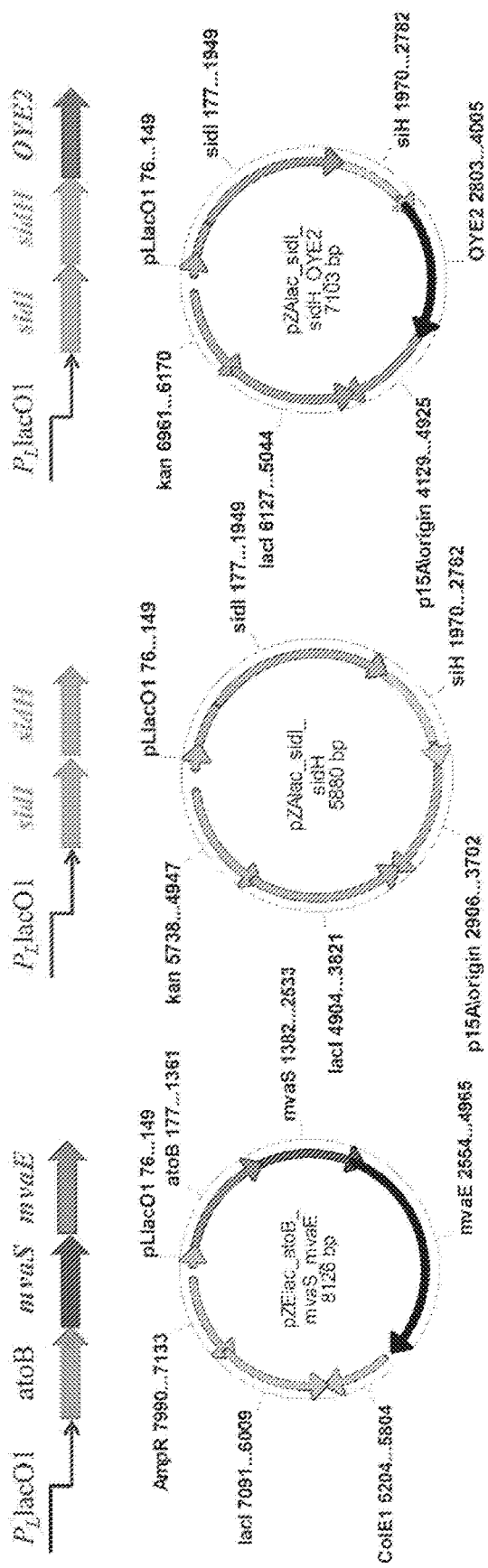
FIG. 9. Plasmids constructed for testing β-methyl-δ-valerolactone (βMδVL) production.

Multiple plasmids have been constructed for the biosynthesis of βMδVL (FIG. 2 and FIG. 9). Plasmid pZElac-atoB-mvaE-mvaS is responsible for mevalonate production. Plasmid pZAlac-sidI-sidH-ter is responsible for converting mevalonate into β-methyl-δ-valerolactone. Plasmid pZAlac-sidI-sidH is responsible for converting mevalonate to anhydromevalonolactone. Plasmid pZAlac-sidI-sidH-OYE2, and variants thereof, are responsible for converting anhydromevalonolactone to β-methyl-δ-valerolactone Primers for plasmid construction are listed in Table 4.

TABLE 4

Primers used

| Primer name | Sequence | SEQ ID NO: |
| --- | --- | --- |
| atoBAcc-F | GGGCCC ggtacc atgAAAAATTGTGTCATCGTCAGTGC | 1 |
| atoBPst-R | GGGCCC ctgcag ttaATTCAACCGTTCAATCACCATCG | 2 |
| mvaSPst-F | GGGCCC ctgcag AGGAGAAATTAACT atgacaattgggattgataaaattag | 3 |
| mvaSBam-R | GGGCCC ggatcc ttagtttcgataagaacgaacggtat | 4 |
| mvaEBam-F | GGGCCC ggatcc AGGAGAAATTAACT atgaaaacagtagttattattgatgc | 5 |
| mvaEXba-R | GGGCCC tctaga ttattgttttcttaaatcatttaaaa | 6 |
| VecAcc-R | GGGCCC ggtacc tttctcctctttaatgaattcggtcagt | 7 |
| VecXba-F | GGGCCC tctaga ggcatcaaataaaacgaaaggctcagtc | 8 |
| SA.mvaSPst-F | GGGCCC ctgcag AGGAGAAATTAACTatgacaataggtatcgacaaaataaa | 9 |
| SA.mvaSBam-R | GGGCCC ggatcc ttactctggtctgtgatattcgcgaa | 10 |
| LC.mvaSPst-F | GGGCCC ctgcag AGGAGAAATTAACTatgaaaatcgggattgatgcaatcgc | 11 |
| LC.mvaSBam-R | GGGCCC ggatcc ttaccgctgctgatattgacgttctt | 12 |
| Bt.mvaSPst-F | GGGCCC ctgcag AGGAGAAATTAACTatgccggtcggtattgaggccatgaa | 13 |
| Bt.mvaSBam-R | GGGCCC ggatcc tTatgaccagacgtactcgcggtgga | 14 |
| Mm.mvaSPst-F | GGGCCC ctgcag AGGAGAAATTAACTatgaaagaagtaggtattgtaggata | 15 |
| Mm.remPst-R | ttagcaccgatgatgtatgcagcaccacc Agcagcagcagtgtattcaagagcatctcc | 16 |
| Mm.remPst-F | ggagatgctcttgaatacactgctgctgc Tggtggtgctgcatacatcatcggtgctaa | 17 |
| Mm.mvaSBam-R | GGGCCC ggatcc ttacattctaattttttcctctgtatttc | 18 |
| Mv.mvaSPst-F | GGGCCC ctgcag AGGAGAAATTAACT atgaacgaagtgggtatcgtaggata | 19 |
| Mv.remPst-R | cctacaagtcccatacacatttgtatacc Agcagtacctgctttacaagcaaattctaa | 20 |
| Mv.remPst-F | ttagaatttgcttgtaaagcaggtactgc Tggtatacaaatgtgtatgggacttgtagg | 21 |
| Mv.mvaSBam-R | GGGCCC ggatcc ttacattctaattttttctctgtatt | 22 |
| Sa.mvaEBam-F | GGGCCC ggatcc AGGAGAAATTAACT atgcaaagtttagataagaatttccg | 23 |
| Sa.mvaEXba-R | GGGCCC tctaga ttattgttgtctaatttcttgtaaaa | 24 |
| Lc.mvaEBam-F | GGGCCC ggatcc AGGAGAAATTAACT atgaaattttacgagttgtctccaga | 25 |
| Lc.mvaEXba-R | GGGCCC tctaga tTaatcccgatttttcatcttttgatt | 26 |
| Mm.mvaEBam-F | GGGCCC ggatcc AGGAGAAATTAACT atggaaaataacgttaatattgaaga | 27 |
| Mm.mvaEXba-R | GGGCCC tctaga ttatcttccaagttcagaatgcgctt | 28 |
| Mv.mvaEBam-F | GGGCCC ggatcc AGGAGAAATTAACT atgaacaatataaaaaataataatga | 29 |
| Mv.mvaEXba-R | GGGCCC tctaga ttaccttcctaattccgaatgtgcgt | 30 |
| pf.sidIAcc-F | GGGCCC ggtacc atggaacactcgggtttccagccgga | 31 |
| pf.sidIHind-R | GGGCCC AAGCTT tTaccccttgttcatgcgctcacgca | 32 |
| bs.sidIACC-F | GGGCCC ggtacc atggctgaactcatccattccacaat | 33 |

TABLE 4-continued

Primers used

| Primer name | Sequence | SEQ ID NO: |
|---|---|---|
| bs.sidIHind-R | GGGCCC AAGCTT tTattgacttgatgataagttgaacatt | 34 |
| re.sidIACC-F | GGGCCC ggtacc atgacgatgcaggccgagtcctctcc | 35 |
| re.sidHind-R | GGGCCC AAGCTT tTaggccgtcctggattcgctgagtt | 36 |
| ec.sidIAcc-F | GGGCCC ggtacc atgGATATCATTGGCGGACAACATCT | 37 |
| ec.sidIHind-R | GGGCCC AAGCTT ttaTTTCAGATTCTTTCTAATTATTT | 38 |
| mm.sidIAcc-F | GGGCCC ggtacc atgattttacaaacgataccatgg | 39 |
| mm.sidIAccrem-R | tggctgtactctgcaataaacatggttggCacccataaagggcagtacacttttcttt | 40 |
| mm.sidIAccrem-F | aaagaaaagtgtactgcccttttatggggtGccaaccatgtttattgcagagtacagcca | 41 |
| mm.sidIHind-R | GGGCCC AAGCTT ttataattcttccgtttctttttttca | 42 |
| terNheI-F | GGGCCCgctagcAGGAGAAATTAACTATGATTATCAAACCGATGATTCGCAG | 43 |
| terBam-R | GGGCCCggatccTTAAACAACGTCCATGCGCTCGACAT | 44 |
| SidHind-F | GGGCCCaagatAGGAGAAATTAACTATGAGCACCGAGGCTCATCCTACTGT | 45 |
| SidHsal-R | GGGCCCgtcgacTTACAACTTGCTCGGGCGCCATTGCG | 46 |
| OYE2sal-F | GGGCCCgtcgacAGGAGAAATTAACTATGCCATTTGTTAAGGACTTTAAGCC | 47 |
| OYE2-Vec | gagcctttcgttttatttgatgcctctagaGCTAGCTTAATTTTTGTCCCAACCGAGTTT | 48 |
| OYE3sal-F | GGGCCCgtcgacAGGAGAAATTAACTATGCCATTTGTAAAAGGTTTTGAGCC | 49 |
| OYE3-Vec | gagcctttcgttttatttgatgcctctagaGCTAGCTtAGTTCTTGTTCCAACCTAAATC | 50 |
| yqjM-F | GGGCCCgtcgacAGGAGAAATTAACTatgGCCAGAAAATTATTTACACCTAT | 51 |
| yqjM-Vec | gagcctttcgttttatttgatgcctctagaGCTAGCTtaCCAGCCTCTTTCGTATTGAAC | 52 |
| yqjMC26D-R | TTCCGTCCTTTTCATGAAGAATACATgtcCATTGGCGACATGACAATGCGGTTTTTT | 53 |
| yqjMC26D-F | AAAAAACCGCATTGTCATGTCGCCAATGgaCATGTATTCTTCTCATGAAAAGGACGGAA | 54 |
| yqjMI69T-R | CGCTCCAAATGCCTAAGTCTTGGTCAGTcgtTCGTCCTTGAGGGTTAACCGCTGACGCC | 55 |
| yqjMI69T-F | GGCGTCAGCGGTTAACCCTCAAGGACGAacgACTGACCAAGACTTAGGCATTTGGAGCG | 56 |

To construct pZElac-atoB-mvaS-mvaE (FIG. 2), the atoB was amplified from *E. coli* genomic DNA with primers atoBAcc-F and atoBPst-R, mvaS was amplified from *Enterococcus faecalis* genomic DNA with primers mvaSPst-F and mvaSBam-R, and mvaE was amplified from *Enterococcus faecalis* genomic DNA with primers mvaE-Bam-F and mvaEXba-R. The vector fragment of pZE was amplified from plasmid pIVC3 (Xiong et al., 2012, *Scientific reports* 2:311) with primers VecAcc-R and VecXba-F. Then the amplified fragments of atoB, mvaS, mvaE and pZE were digested with Acc65I/PstI, PstI/BamHI, BamHI/XbaI, and Acc65I/XbaI, respectively. These digested fragments were ligated with T4 DNA ligase to form plasmid pZElac-atoB-mvaS-mvaE.

To build plasmids with combinations of different mvaS and mvaE, mvaS genes from *S. aureus, L. casei, M maripaludis* and *M. voltae* were amplified from their corresponding genomic DNA with primer pairs SA.mvaSPst-F/SA.mvaSBam-R, LC.mvaSPst-F/LC.mvaSBam-R, Mm.mvaSPst-F/Mm.remPst-R and Mm.remPst-F/Mm.mvaSBam-R, Mv.mvaSPst-F/Mv.remPst-R and Mv.remPst-F/Mv.mvaS-Bam-R, respectively. Then mvaS in plasmid pMEV-1 was replaced to form plasmids pZElac-atoB-Sa.mvaS-mvaE, pZElac-atoB-Lc.mvaS-mvaE, pZElac-atoB-Bt.mvaS-mvaE, pZElac-atoB-Mm.mvaS-mvaE and pZElac-atoB-Mv.mvaS-mvaE.

Since the transformed *E. coli* strain with plasmid pZElac-atoB-Lc.mvaS-mvaE produced the highest level of MEV, more plasmids were constructed with different mvaE based on pMEV-3. mvaE genes from *S. aureus, L. casei, M. maripaludis* and *M. voltae* were amplified from their corresponding genomic DNA with primer pairs Sa.mvaEBam-F/Sa.mvaEXba-R, Lc.mvaEBam-F/Lc.mvaEXba-R, Mm.mvaEBam-F/Mm.mvaEXba-R, and Mv.mvaEBam-F/Mv.mvaEXba-R, respectively. Then mvaE in plasmid pZElac-atoB-Lc.mvaS-mvaE was replaced to form pZElac-atoB-Lc.mvaS-Sa.mvaE, pZElac-atoB-Lc.mvaS-Lc.mvaE, pZElac-atoB-Lc.mvaS-Mm.mvaE and pZElac-atoB-Lc.mvaS-Mv.mvaE.

To build plasmid pZAlac-sidI-sidH-ter, sidI and sidH from *Aspergillus fumigatus* were codon-optimized and synthesized by Integrated DNA Technologies, Inc. (Coralville, Iowa). Then, sidI and sidH digested with Acc65I-HindIII, and HindIII-NheI, respectively, were inserted into the corresponding sites in plasmid pIVC1 (Xiong et al., 2012, *Scientific reports* 2:311) to from pZAlac-sidI-sidH. The gene ter was PCR amplified by primer pair terNhe-F/terBam-R using *T. denticola* genomic DNA (Shen et al., 2011, *Appl Environ Microbiol* 77:2905-2915) as the template. The ter fragment was inserted into the corresponding sites of plasmid pZAlac-sidI-sidH to form pZAlac-sidI-sidH-ter.

To build a plasmid for synthesizing anhydromevalonolactone, sidI and sidH from *Aspergillus fumigatus, Neurospora crassa, Phaeosphaeria nodorum*, and *Sclerotinia sclerotiorum* (Grundlinger et al., 2013, *Mol Microbiol* 88:862-875) were codon-optimized and synthesized by GenScript USA, Inc. (Tulsa, Okla.). Then, sidI and sidH, digested with Acc65I-HindIII and HindIII-NheI, respectively, were inserted into the corresponding sites in plasmid pIVC1 (Xiong et al., 2012, *Scientific reports* 2:311) to form pZAlac-afsidI-afsidH, pZAlac-ncsidI-ncsidH, pZAlac-pnsidI-pnsidH and pZAlac-sssidI-sssidH, respectively.

To build pZAlac-sidI-sidH-OYE2, sidH was PCR amplified with primers SidHind-F and SidHsal-R using plasmid pZAlac-sidI-sidH as a template. OYE2 was PCR amplified with primers OYE2sal-F and OYE2-Vec using *S. cerevisiae* genomic DNA as template. The amplified sidH was digested with HindIII and SalI; OYE2 was digested with SalI and NheI, then used to replace sidH in the plasmid pZAlac-afsidI-afsidH to form pZAlac-afsidI-afsidH-OYE2.

To build additional variant plasmids, OYE3 was PCR amplified with primers OYE3sal-F and OYE3-Vec using genomic DNA of *S. cerevisiae* as a template. YqjM was PCR amplified with primers yqjM-F and yqjM-Vec using genomic DNA of *B. subtilis* as template. The amplified OYE3 was used to replace OYE2 of pZAlac-sidI-sidH-OYE2 to generate pZAlac-sidI-sidH-OYE3. The amplified YqjM was used to replace OYE2 of pZAlac-sidI-sidH-OYE2 to generate pZAlac-afsidI-afsidH-YqjM.

To introduce two point mutants inside the YqjM coding region, three fragments were PCR amplified with primer pairs of yqjM-F/yqjMC26D-R, yqjMC26D-F/yqjMI69T-R, and yqjMI69T-F/yqjM-Vec using *B. subtilis* genomic DNA as template. Another round of PCR was carried out with primers yqjM-F and yqjM-vec using the last three PCR fragments as template. The PCR product was used to replace OYE2 of pZAlac-afsidI-afsidH-OYE2 to generate pZAlac-afsidI-afsidH-YqjM(mt).

Shake Flask Fermentation

To carry out small-scale fermentation, 125 mL conical flasks with 0.5 g $CaCO_3$ was autoclaved and dried. Then the flasks were filled with 5 mL M9 medium supplemented with 5 g/L yeast extract, 40 g/L glucose, and antibiotics. 200 µL of overnight cultures incubated in 2× YT medium were transferred into the flasks and placed in a shaker at a speed of 250 rpm. After adding 0.1 mM isopropyl-β-D-thiogalactoside (IPTG), the fermentation was performed for 48 hours at 30° C.

Fed-Batch Fermentation in Bio-Reactor

Fermentation media for bioreactor cultures contained the following composition, in grams per liter: glucose, 10; $K_2HPO_4$, 7.5; citric acid monohydrate, 2.0; yeast extract, 0.5; $MgSO_4.7H_2O$, 2.0; Thiamine hydrochloride, 0.008; D-(+)-biotin, 0.008; nicotinic acid, 0.008; pyridoxine, 0.032; ampicillin, 0.1; concentrated $H_2SO_4$, 0.8 mL; and 1 mL/L of trace metal solution. Trace metal solution contained, in grams per liter: NaCl, 10; Citric acid, 40; $ZnSO_4.7H_2O$, 1.0; $MnSO_4.H_2O$, 30; $CuSO_4.5H_2O$, 0.1; $H_3BO_3$, 0.1; $Na2MoO4.2H_2O$, 0.1; $FeSO_4.7H_2O$, 1.0; $CoCl_2.6H_2O$, 1.0. The feeding solution contained, in grams per liter: glucose, 600; $K_2HPO_4$, 7.4; and 10 mL antifoam.

Cultures of *E. coli* were performed in 1.3 L Bioflo 115 Fermentor (NBS, Edison, N.J.) using an initial working volume of 0.5 L. The fermentor was inoculated with 10% of overnight pre-culture with 2× YT medium. The culturing condition was set at 34° C., dissolved oxygen level (DO) 30%, and pH 7.0. After $OD_{600}$ reached 6.0, 0.2 mM IPTG was added to produce mevalonate. The pH was controlled at 7.0 by automatic addition of 26% ammonia hydroxide. Air flow rate was maintained at 1 vvm in the whole process. DO was maintained about 20% with respect to air saturation by raising stirrer speed (from 300 to 1200 rpm). The fed-batch rate of glucose was determined according to the glucose consumption rate manually. The fermentation process was stopped two days after IPTG addition. Fermentation culture was sampled periodically to determine cell density and production level.

Chemical Reaction and Extraction

The fermentation broth from the bioreactor was harvested by centrifuge, and then was discolored by activated charcoal. The test tubes were filled with 5 mL fermentation broth and concentrated $H_3PO_4$ or $H_2SO_4$, then autoclaved for one hour to make anhydromevalonate, and then the concentrations of mevalonate and anhydromevalonate were measured by HPLC. Immiscible organic solvents were used to extraction anhydromevalonate from the reaction mixture.

Metabolite Analysis and Cell Dry Weight Determination

Fermentation products were analyzed using an Agilent 1260 Infinity HPLC (Agilent Technologies, Inc., Santa Clara, Calif.) equipped with an Aminex HPX 87H column (Bio-Rad Laboratories, Inc., Hercules, Calif.) and a refractive-index detector (Agilent Technologies, Inc., Santa Clara, Calif. The mobile phase was 0.01N $H_2SO_4$ with a flow rate of 0.6 mL/min. The column temperature and detection temperature were 35° C. and 50° C., respectively. Cell dry weight was determined by filtering 5 mL of culture through a 0.45 µm pre-weighed glass fiber filter. After removal of medium, the filter was washed with 15 mL of distilled de-ionized water, dried in a microwave oven for 20 minutes at 300 W, and then weighed. Cell dry weight was determined in triplicate.

Fermentation Scale-Up from 1 L to 500 L

Fermentation media for bioreactor cultures contained the following composition: 10 g/L glucose, 7.5 g/L $K_2HPO_4$, 2.0 g/L citric acid monohydrate, 0.5 g/L yeast extract, 2.0 g/L $MgSO_4.7H_2O$, 0.008 g/L thiamine hydrochloride, 0.008 g/L D-(+)-biotin, 0.008 g/L nicotinic acid, 0.032 g/L pyridoxine, 0.1 g/L ampicillin, 0.8 mL concentrated $H_2SO_4$, and 1 mL/L of trace metal solution (10 g/L NaCl, 40 g/L citric acid, 1.0 g/L $ZnSO_4.7H_2O$, 30 g/L $MnSO_4.H_2O$, 0.1 g/L $CuSO_4.5H_2O$, 0.1; $H_3BO_3$, 0.1 g/L $Na_2MoO_4.2H_2O$, 1.0 g/L $FeSO_4.7H_2O$, and 1.0 g/L $CoCl_2.6H_2O$). The feed solution contained: 600 g/L glucose, 7.4 g/L $K_2HPO_4$, and 10 mL antifoam. The 500 L culture conditions were pH 6.8 and a temperature of 34° C.

A culture of *E. coli* BW25113 was aseptically transferred into a 250 mL baffled shake flask containing 50 mL of 2× YT seed medium (S0 culture). The culture was incubated for eight hours at 34° C. and 200 rpm, and then 30 mL of the S0 culture was used to inoculate a 6 L baffled shake flask containing two liters sterile 2× YT medium. The culture was incubated at 34° C. and 200 rpm for five hours. After the five-hour incubation, the entire contents of the flask was used to inoculate the 75 L bioreactor (New Brunswick Scientific, Eppendorf, Inc., Enfield Conn.). The culture was transferred from the 75 L bioreactor to a 550 L bioreactor (DCI-Biolafitte, St. Cloud, Minn.) through a steam sterilized transfer line after four hours. At 3.5 hours, the $OD_{600}$ reached 6.80 at which time the culture was induced with IPTG (final concentration of 0.4 mM). The feed was started at this time. The glucose was fed exponentially for 9.25 hours of the run using the equation below.

$$\text{Feed Rate } (L/h) = (CDW^* V^* \mu_{max} e^{\mu_{max}*t})/(\text{Feed Conc.}^*\text{Cell Yield})$$

Parameters used: CDW=1 g/L; V=200 L; $\mu_{max}$=0.27; Feed Conc.=600 g/L; Cell Yield=0.45 g/g, and t=EFT.

The glucose levels were monitored by using an off-line monitor (YSI, Inc., Yellow Springs, Ohio). The exponential was changed to 0.35 at 9.75 hours to help control the culture glucose concentration at 5-10 g/L.

At 6.75, 7.75 and 8.75 hours EFT, the agitation was set to 250 rpm, the airflow to 200 slpm and the back pressure to 15 psi to control dissolved oxygen levels. At 9.75 EFT, the feed exponential was increased to 0.29 to keep glucose at the desired level. At 10.25 EFT, the dissolved oxygen control was turned on and set to 15%, initially, and later set to 20% for the remainder of the run. The feed pump was varied at each time point to try and maintain glucose between 5-10 g/L. After observing flat culture growth and slowing glucose consumption, the reactor was cooled and prepared for harvest at 36 hours EFT.

Figure 10:
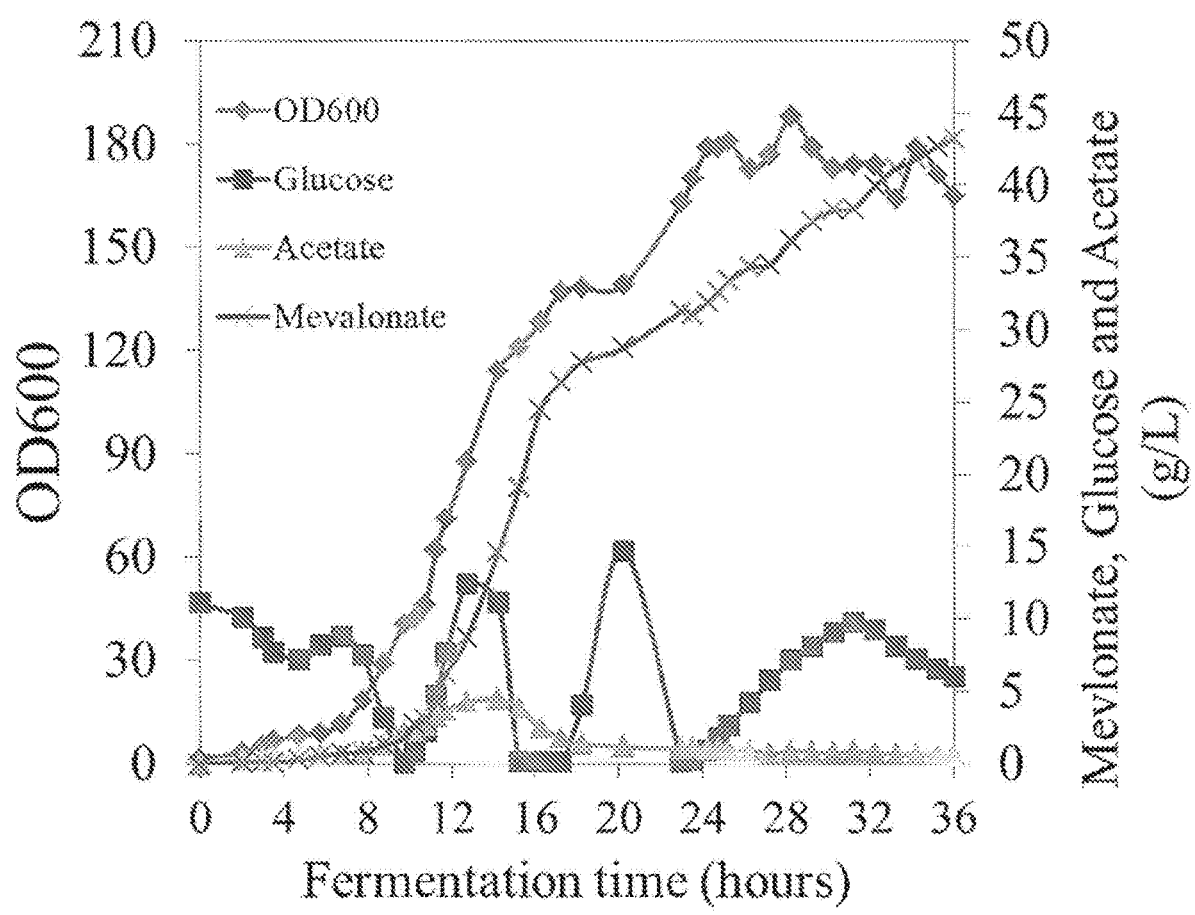
FIG. 10. 500 L fermentation curve.

The concentrations of glucose, acetate, mevalonate and biomass are shown in FIG. 10.

Example 2

Bacterial and Growth Conditions

BW25113 (rrnB$_{T14}$ $\Delta$lacZ$_{WJ16}$ hsdR514 $\Delta$araBAD$_{AH33}$ $\Delta$rhaBAD$_{LD78}$) was used to produce mevalonate (MEV) and β-methyl-δ-valerolactone (βMδVL). (Datsenko et al., 2000, Proc Natl Acad Sci USA 97:6640-6645) All cloning procedures were carried out in the E. coli strain XL10-gold (Stratagene, Agilent Technologies, Inc., Santa Clara, Calif.). These E. coli strains were grown in test tubes at 37° C. in 2× YT rich medium (16 g/L Bacto-tryptone, 10 g/L yeast extract and 5 g/L NaCl) supplemented with appropriate antibiotics (ampicillin 100 µg/mL and kanamycin 50 µg/mL) unless otherwise specified.

Plasmid Construction

Three plasmids were constructed for the biosynthesis of βMδVL (FIG. 9). The first plasmid, pMEV-1, is responsible for MEV production. The second plasmid, pAML-1, is used to produce anhydromevalonolactone (AML); the third plasmid is used to convert AML into βMδVL. Primers for plasmid construction are those listed above in Table 4.

To construct pMEV-1 (FIG. 9), atoB was amplified from E. coli genomic DNA with primers atoBAcc-F and atoBPst-R, and mvaS and mvaE were amplified from E. faecalis genomic DNA with primers mvaSPst-F and mvaSBam-R, mvaEBam-F and mvaEXba-R. The vector fragment of pZE was amplified from plasmid pIVC3 (Xiong et al., 2012, Scientific reports 2:311) with primers VecAcc-R and VecXba-F. Then the amplified fragments of atoB, mvaS, mvaE and pZE were digested with Acc65I/PstI, PstI/BamHI, BamHI/XbaI, and Acc65I/XbaI, respectively. These digested genes were ligated with T4 DNA ligase to form the plasmid pMEV-1.

To build plasmids with combinations of different mvaS and mvaE, mvaS genes from S. aureus, L. casei, M maripaludis and M. voltae were amplified from their corresponding genomic DNA with primer pairs SA.mvaSPst-F/SA.mvaSBam-R, LC.mvaSPst-F/LC.mvaSBam-R, Mm.mvaSPst-F/Mm.remPst-R and Mm.remPst-F/Mm.mvaSBam-R, Mv.mvaSPst-F/Mv.remPst-R and Mv.remPst-F/Mv.mvaS-Bam-R, respectively. Then mvaS in plasmid pMEV-1 was replaced to form plasmids of pMEV-2, pMEV-3, pMEV-4, and pMEV-5, respectively.

Since the transformed E. coli strain with plasmid pMEV-3 produced the highest level of MEV, more plasmids were constructed with different mvaE based on pMEV-3. mvaE genes from S. aureus, L. casei, M. maripaludis and M. voltae were amplified from their corresponding genomic DNA with primer pairs Sa.mvaEBam-F/Sa.mvaEXba-R, Lc.mvaEBam-F/Lc.mvaEXba-R, Mm.mvaEBam-F/Mm.mvaEXba-R, and Mv.mvaEBam-F/Mv.mvaEXba-R, respectively. Then mvaE in plasmid pMEV-3 was replaced to form pMEV-6, pMEV-7, pMEV-8, and pMEV-9, respectively.

To build plasmids to synthesize anhydromevalonolactone (AML), sidI and sidH from A. fumigatus, N crassa, P. nodorum, S. sclerotiorum (Grundlinger et al., 2013, Mol Microbiol 88:862-875) were codon-optimized and synthesized by GenScript USA, Inc. (Tulsa, Okla.). Then, sidI and sidH, digested with Acc65I/HindIII and HindIII/NheI, were inserted into the corresponding sites in plasmid pIVC1 (Xiong et al., 2012, Scientific reports 2:311) to form pAML-1, pAML-2, pAML-3 and pAML-4, respectively.

To build pMVL-1, sidH was PCR amplified with primers SidHind-F and SidHsal-R and using plasmid pAML-1 as a template. OYE2 was PCR amplified with primers OYE2sal-F and OYE2-Vec using S. cerevisiae genomic DNA as template. The amplified sidH was digested with HindIII and SalI; OYE2 was digested with SalI and NheI, then used to replace sidH in the plasmid pAML-1 to form pMVL-1.

To build pMVL-2, OYE3 was PCR amplified with primers OYE3sal-F and OYE3-Vec using genomic DNA of S. cerevisiae as a template. The amplified OYE3 was used to replace OYE2 of pMVL-1 to generate pMVL-2.

To build pMVL-3, YqjM was PCR amplified with primers yqjM-F and yqjM-Vec using genomic DNA of B. subtilis as template. The amplified YqjM was used to replace OYE2 of pMVL-1 to generate pMVL-3.

To introduce two point mutants into yqjM, three fragments were PCR amplified with primers yqjM-F/yqjMC26D-R, yqjMC26D-F/yqjMI69T-R and yqjMI69T-F/yqjM-Vec using B. subtilis genomic DNA as the template. Another round PCR was carried out with primers yqjM-F and yqjM-vec by using the last three PCR fragments as templates. The PCR product was inserted into pAML-1 to generate pMVL-4.

Shake Flask Batch Fermentation

To carry out small-scale fermentation, 125-mL conical flasks with 0.5 g CaCO$_3$ were autoclaved and dried. The flasks were filled with 5 mL M9 medium supplemented with 5 g/L yeast extract, 40 g/L glucose and antibiotics. 200 µL of overnight cultures that had been incubated in 2× YT medium were transferred into the flasks and placed in a shaker at a speed of 250 rpm. After adding 0.1 mM isopropyl-β-D-thiogalactoside (IPTG), the fermentation was performed for 48 hours at 30° C. The fermentation results for mevalonate production, anhydromevalonolactone production, and β-methyl-δ-valerolactone production in shake flasks are provided in Tables 5-7.

TABLE 5

Batch fermentation results for mevalonate production

| Strain | Acetate (g/L)* | MEV (g/L)* |
|---|---|---|
| BW25113 with pMEV-1 | 0.45 ± 0.28 | 10.75 ± 0.28 |
| BW25113 with pMEV-2 | 3.11 ± 0.07 | 5.05 ± 0.28 |

TABLE 5-continued

Batch fermentation results for mevalonate production

| Strain | Acetate (g/L)* | MEV (g/L)* |
|---|---|---|
| BW25113 with pMEV-3 | 0.20 ± 0.03 | 12.57 ± 0.15 |
| BW25113 with pMEV-4 | 6.48 ± 0.49 | 0 |
| BW25113 with pMEV-5 | 8.80 ± 1.51 | 0 |
| BW25113 with pMEV-6 | 0.13 ± 0.05 | 13.37 ± 0.54 |
| BW25113 with pMEV-7 | 0.17 ± 0.01 | 14.62 ± 0.24 |
| BW25113 with pMEV-8 | 0.13 ± 0.05 | 10.90 ± 0.39 |
| BW25113 with pMEV-9 | 0.18 ± 0.02 | 11.48 ± 0.28 |

*n = 3, data are shown as mean ± s.d.

TABLE 6

Batch fermentation results for anhydromevalonolactone production

| Strain | MEV (g/L)* | AML (g/L)* |
|---|---|---|
| BW25113 with pMEV-7 and pAML-1 | 12.36 ± 1.18 | 0.73 ± 0.06 |
| BW25113 with pMEV-7 and pAML-2 | 13.59 ± 0.24 | 0.54 ± 0.02 |

*n = 3, data are shown as mean ± s.d.

TABLE 7

Batch fermentation results for βMδVL production

| Strain | MEV (g/L)* | AML (g/L)* | βMδVL (g/L)* |
|---|---|---|---|
| BW25113 with pMEV-7 and pMVL-1 | 10.19 ± 0.61 | 0.34 ± 0.03 | 0.18 ± 0.03 |
| BW25113 with pMEV-7 and pMVL-2 | 6.77 ± 0.58 | 0.48 ± 0.03 | 0 |
| BW25113 with pMEV-7 and pMVL-3 | 8.85 ± 0.56 | 0.55 ± 0.01 | 0 |
| BW25113 with pMEV-7 and pMVL-4 | 9.39 ± 0.48 | 0.31 ± 0.01 | 0.27 ± 0.02 |

*n = 3, data are shown as mean ± s.d.

Fed-Batch Fermentation in Bioreactor

Fermentation media for bioreactor cultures contained the following composition: 10 g/L glucose, 7.5 g/L $K_2HPO_4$, 2.0 g/L citric acid monohydrate, 0.5 g/L yeast extract, 2.0 g/L $MgSO_4 \cdot 7H_2O$, 0.008 g/L thiamine hydrochloride, 0.008 g/L D-(+)-biotin, 0.008 g/L nicotinic acid, 0.032 g/L pyridoxine, 0.1 g/L ampicillin, 0.8 mL concentrated $H_2SO_4$, and 1 mL/L of trace metal solution (10 g/L NaCl, 40 g/L citric acid, 1.0 g/L $ZnSO_4 \cdot 7H_2O$, 30 g/L $MnSO_4 \cdot H_2O$, 0.1 g/L $CuSO_4 \cdot 5H_2O$, 0.1; $H_3BO_3$, 0.1 g/L $Na_2MoO_4 \cdot 2H_2O$, 1.0 g/L $FeSO_4 \cdot 7H_2O$, and 1.0 g/L $CoCl_2 \cdot 6H_2O$). The feed solution contained: 600 g/L glucose, 7.4 g/L $K_2HPO_4$, and 10 mL antifoam.

E. coli cultures were grown in 1.3-L BIOFLO 115 Fermentor (New Brunswick Scientific, Eppendorf, Inc., Enfield Conn.) using an initial working volume of 0.5 L. The fermenter was inoculated with 10% of overnight pre-culture with 2× YT medium. The culture conditions were set at 34° C., dissolved oxygen level (DO) 30%, and pH 7.0. After $OD_{600}$ reached 5.2, 0.2 mM IPTG was added to produce mevalonate (MEV). The pH was controlled at 7.0 by automatic addition of 26% ammonium hydroxide. Airflow rate was maintained at 1 vvm throughout the process. Dissolved oxygen was maintained about 20% with respect to air saturation by raising stirring speed (from 300 rpm to 1200 rpm). The fed-batch rate of glucose was determined according to the glucose consumption rate manually. The fermentation process was stopped two days after the IPTG was added. The fermentation culture was sampled periodically to determine cell density and production level. The detailed fermentation results are listed in Table 8.

TABLE 8

Fed-batch fermentation results for the production of mevalonate in 1.3 L bioreactor

| Time (h) | Biomass (g/L) | Glucose (g/L) | Acetate (g/L) | MEV (g/L) |
|---|---|---|---|---|
| 0 | 1.3 | 4.6 | 0.85 | 0 |
| 5.5 | 6.9 | 12.9 | 2.25 | 1.7 |
| 16 | 30.0 | 0 | 1.39 | 24.5 |
| 19 | 34.0 | 14.3 | 0.48 | 34.4 |
| 24.5 | 37.8 | 24.8 | 0.35 | 40.5 |
| 31 | 29.8 | 34.2 | 0.33 | 50.0 |
| 40.5 | 27.0 | 27.3 | 1.09 | 69.6 |
| 43 | 24.5 | 12.5 | 1.50 | 77.1 |
| 48 | 24.0 | 0 | 3.48 | 88.3 |

Dehydration and Extraction

Figure 5A:
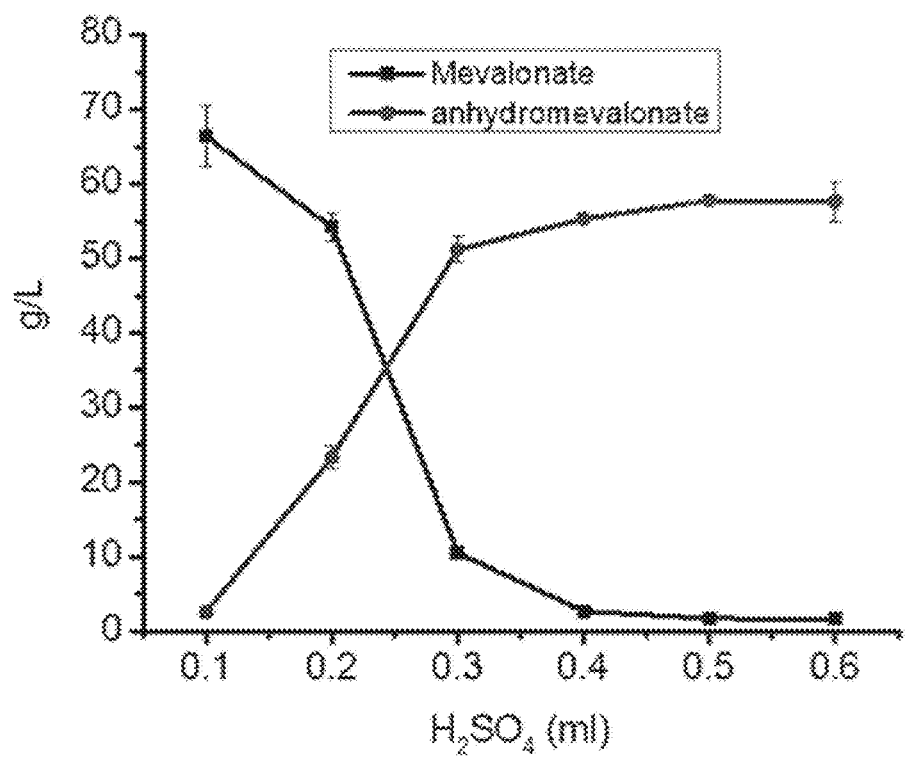
FIG. 5. Dehydration of mevalonate fermentation sample to anhydromevalonolactone catalyzed by sulfuric acid. (A) reaction with different sulfuric acid concentration. (B) HPLC measurement.
Figure 5B:
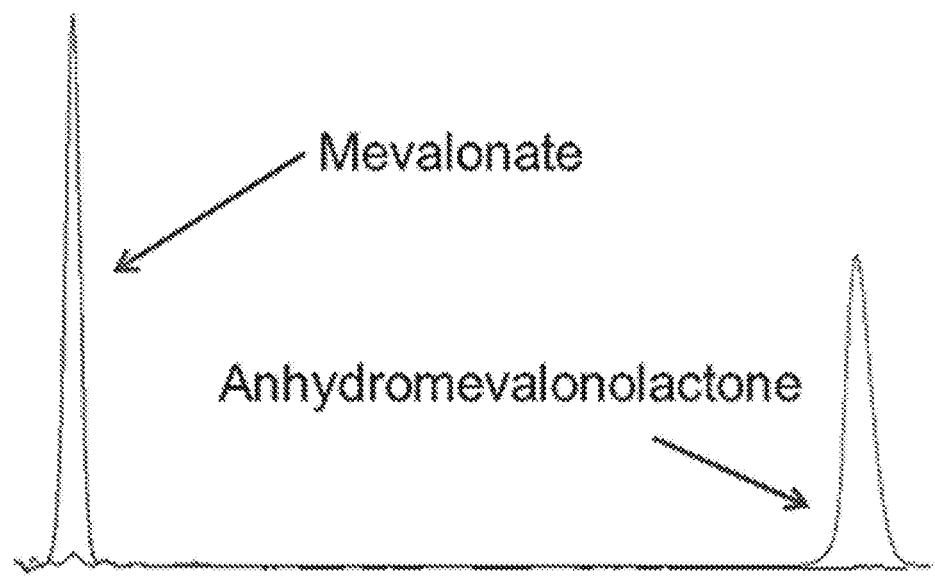

The fermentation broth from bioreactor was harvested by centrifugation, then filtered through activated charcoal to remove colored contaminants. To determine the optimal level of catalyst for the dehydration, reaction test tubes were filled with 5 mL fermentation broth and 0-12% concentrated $H_2SO_4$, then autoclaved for one hour (121° C., 15 psi) to produce anhydromevalonolactone. The concentrations of mevalonate (MEV) and anhydromevalonolactone (AML) were measured by HPLC. Chloroform was used to extract AML from the reaction mixture. The results of dehydration are shown in FIG. 5A and Table 9.

TABLE 9

Dehydration results by using different concentration of $H_2SO_4$

| $H_2SO_4$ (%) | MEV (g/L)* | AML (g/L)* | Conversion (%)* | Selectivity (%)* |
|---|---|---|---|---|
| 0 | 88.3 | 0 | — | — |
| 2 | 66.9 ± 4.2 | 2.5 ± 0.7 | 24.2 ± 4.7 | 15.5 ± 1.3 |
| 4 | 54.6 ± 1.8 | 23.5 ± 1.6 | 38.2 ± 2.0 | 91.9 ± 1.3 |
| 6 | 10.6 ± 0.1 | 51.6 ± 1.8 | 88.0 ± 0.1 | 87.7 ± 3.1 |
| 8 | 2.7 ± 0.1 | 55.7 ± 0.7 | 97.0 ± 0.1 | 86.0 ± 0.9 |
| 10 | 1.7 ± 0.0 | 58.2 ± 0.6 | 98.1 ± 0.0 | 88.8 ± 0.9 |
| 12 | 1.6 ± 0.0 | 58.1 ± 2.7 | 98.2 ± 0.0 | 88.5 ± 4.2 |

*n = 3, data are shown as mean ± s.d.

Metabolite Analysis and Cell Dry Weight Determination

Fermentation products were analyzed using an Agilent 1260 Infinity HPLC (Agilent Technologies, Inc., Santa Clara, Calif.) equipped with an Aminex HPX 87H column (Bio-Rad Laboratories, Inc., Hercules, Calif.) and a refractive-index detector (Agilent Technologies, Inc., Santa Clara, Calif. The mobile phase was 0.01N $H_2SO_4$ with a flow rate of 0.6 mL/min. The column temperature and detection temperature were 35° C. and 50° C., respectively. Cell dry weight was determined by filtering 5 mL of culture through a 0.45 µm pre-weighed glass fiber filter. After removal of medium, the filter was washed with 15 mL of distilled de-ionized water, dried in a microwave oven for 20 minutes at 300 W, and then weighed. Cell dry weight was determined in triplicate.

Hydrogenation

Unreduced palladium on activated carbon (10% w/w; Acros Organics, Thermo Fisher Scientific, Inc., Waltham, Mass.) was dried in situ prior to use. Tetrahydrofuran (THF) (Fisher Chemical, Thermo Fisher Scientific, Inc., Waltham, Mass.) was used as received. In a typical hydrogenation procedure, 10 g of catalyst were added to a 300 mL high-pressure reactor with jacketed temperature control and mechanical stirring. The palladium catalyst was held under vacuum at 80° C. for an hour, then cooled to ambient temperature.

Separately, 50 mL of anhydromevalonate was transferred into a solution delivery vessel and sparged with argon for at least 15 minutes. The solution delivery vessel was attached to the reactor and 50 psig argon was applied to displace the contents into the cooled reactor. The argon was released, and the solution delivery vessel detached, stirring was initiated, and the vessel was charged with $H_2$ to a pressure of approximately 350 psig. The pressure in the vessel was replenished periodically as the hydrogenation progressed until the pressure remained static within the vessel. The reaction was then allowed to stir under $H_2$ at room temperature overnight to ensure quantitative conversion.

Following depressurization, the reactor was flushed with argon and the reactor contents diluted with THF to facilitate total transfer. The catalyst was removed from the solution by filtration through a filter flask containing a 0.45 μm HVHP membrane (Millipore Corp., Billerica, Mass.). The THF was removed by rotary evaporation to obtain crude β-methyl-δ-valerolactone in typical yields of approximately 93% (conversion >99% by $^1$HNMR).

β-methyl-δ-valerolactone Purification

Basic alumina (60-325 mesh, Thermo Fisher Scientific, Inc., Waltham, Mass.) was dried under vacuum at 300° C. for three hours, then cooled under argon. Cyclohexane was passed through a solvent purification system, which included a column of activated alumina and a column of molecular sieves operated under a positive pressure of nitrogen gas. The crude β-methyl-δ-valerolactone was dried over calcium hydride ($CaH_2$) powder (Sigma-Aldrich, St. Louis, Mo.) for 12 hours then distilled under vacuum (50 mTorr, 30° C.). The distilled product was passed through dry basic alumina using cyclohexane as an eluent. The cyclohexane was removed under vacuum to obtain purified β-methyl-δ-valerolactone.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A composition comprising anhydromevalonolactone or anhydromevalonate comprising a $^{14}C/^{12}C$ ratio greater than zero.

2. The composition of claim 1, wherein the $^{14}C/^{12}C$ ratio is greater than $0.25 \times 10^{-12}$.

3. The composition of claim 1, wherein the $^{14}C/^{12}C$ ratio is from $0.25 \times 10^{-12}$ to $1.2 \times 10^{-12}$.

* * * * *

SEQUENCE LISTING

```
<160> NUMBER OF SEQ ID NOS: 62

<210> SEQ ID NO 1
<211> LENGTH: 38
<212> TYPE: DNA
<213> ORGANISM: artificial
<220> FEATURE:
<223> OTHER INFORMATION: synthetic oligonucleotide primer

<400> SEQUENCE: 1
gggcccggta ccatgaaaaa ttgtgtcatc gtcagtgc                               38

<210> SEQ ID NO 2
<211> LENGTH: 38
<212> TYPE: DNA
<213> ORGANISM: artificial
<220> FEATURE:
<223> OTHER INFORMATION: synthetic oligonucleotide primer

<400> SEQUENCE: 2
gggcccctgc agttaattca accgttcaat caccatcg                              38

<210> SEQ ID NO 3
<211> LENGTH: 52
```

<210> SEQ ID NO 3
<211> LENGTH: 52
<212> TYPE: DNA
<213> ORGANISM: artificial
<220> FEATURE:
<223> OTHER INFORMATION: synthetic oligonucleotide primer

<400> SEQUENCE: 3
gggcccctgc agaggagaaa ttaactatga caattgggat tgataaaatt ag          52

<210> SEQ ID NO 4
<211> LENGTH: 38
<212> TYPE: DNA
<213> ORGANISM: artificial
<220> FEATURE:
<223> OTHER INFORMATION: synthetic oligonucleotide primer

<400> SEQUENCE: 4
gggcccggat ccttagtttc gataagaacg aacggtat                          38

<210> SEQ ID NO 5
<211> LENGTH: 52
<212> TYPE: DNA
<213> ORGANISM: artificial
<220> FEATURE:
<223> OTHER INFORMATION: synthetic oligonucleotide primer

<400> SEQUENCE: 5
gggcccggat ccaggagaaa ttaactatga aaacagtagt tattattgat gc          52

<210> SEQ ID NO 6
<211> LENGTH: 38
<212> TYPE: DNA
<213> ORGANISM: artificial
<220> FEATURE:
<223> OTHER INFORMATION: synthetic oligonucleotide primer

<400> SEQUENCE: 6
gggccctcta gattattgtt ttcttaaatc atttaaaa                          38

<210> SEQ ID NO 7
<211> LENGTH: 40
<212> TYPE: DNA
<213> ORGANISM: artificial
<220> FEATURE:
<223> OTHER INFORMATION: synthetic oligonucleotide primer

<400> SEQUENCE: 7
gggcccggta cctttctcct ctttaatgaa ttcggtcagt                        40

<210> SEQ ID NO 8
<211> LENGTH: 40
<212> TYPE: DNA
<213> ORGANISM: artificial
<220> FEATURE:
<223> OTHER INFORMATION: synthetic oligonucleotide primer

<400> SEQUENCE: 8
gggccctcta gaggcatcaa ataaaacgaa aggctcagtc                        40

<210> SEQ ID NO 9
<211> LENGTH: 52
<212> TYPE: DNA
<213> ORGANISM: artificial
<220> FEATURE:
<223> OTHER INFORMATION: synthetic oligonucleotide primer

<400> SEQUENCE: 9
gggcccctgc agaggagaaa ttaactatga caataggtat cgacaaaata aa         52

<210> SEQ ID NO 10
<211> LENGTH: 38
<212> TYPE: DNA
<213> ORGANISM: artificial
<220> FEATURE:
<223> OTHER INFORMATION: synthetic oligonucleotide primer

<400> SEQUENCE: 10
gggcccggat ccttactctg gtctgtgata ttcgcgaa                         38

<210> SEQ ID NO 11
<211> LENGTH: 52
<212> TYPE: DNA
<213> ORGANISM: artificial
<220> FEATURE:
<223> OTHER INFORMATION: synthetic oligonucleotide primer

<400> SEQUENCE: 11
gggcccctgc agaggagaaa ttaactatga aaatcgggat tgatgcaatc gc         52

<210> SEQ ID NO 12
<211> LENGTH: 38
<212> TYPE: DNA
<213> ORGANISM: artificial
<220> FEATURE:
<223> OTHER INFORMATION: synthetic oligonucleotide primer

<400> SEQUENCE: 12
gggcccggat ccttaccgct gctgatattg acgttctt                         38

<210> SEQ ID NO 13
<211> LENGTH: 52
<212> TYPE: DNA
<213> ORGANISM: artificial
<220> FEATURE:
<223> OTHER INFORMATION: synthetic oligonucleotide primer

<400> SEQUENCE: 13
gggcccctgc agaggagaaa ttaactatgc cggtcggtat tgaggccatg aa         52

<210> SEQ ID NO 14
<211> LENGTH: 38
<212> TYPE: DNA
<213> ORGANISM: artificial
<220> FEATURE:
<223> OTHER INFORMATION: synthetic oligonucleotide primer

<400> SEQUENCE: 14
gggcccggat ccttatgacc agacgtactc gcggtgga                         38

<210> SEQ ID NO 15
<211> LENGTH: 52
<212> TYPE: DNA
<213> ORGANISM: artificial
<220> FEATURE:
<223> OTHER INFORMATION: synthetic oligonucleotide primer

<400> SEQUENCE: 15
gggcccctgc agaggagaaa ttaactatga aagaagtagg tattgtagga ta         52

<210> SEQ ID NO 16
<211> LENGTH: 59
<212> TYPE: DNA
<213> ORGANISM: artificial

```
<220> FEATURE:
<223> OTHER INFORMATION: synthetic oligonucleotide primer

<400> SEQUENCE: 16
ttagcaccga tgatgtatgc agcaccacca gcagcagcag tgtattcaag agcatctcc      59

<210> SEQ ID NO 17
<211> LENGTH: 59
<212> TYPE: DNA
<213> ORGANISM: artificial
<220> FEATURE:
<223> OTHER INFORMATION: synthetic oligonucleotide primer

<400> SEQUENCE: 17
ggagatgctc ttgaatacac tgctgctgct ggtggtgctg catacatcat cggtgctaa      59

<210> SEQ ID NO 18
<211> LENGTH: 40
<212> TYPE: DNA
<213> ORGANISM: artificial
<220> FEATURE:
<223> OTHER INFORMATION: synthetic oligonucleotide primer

<400> SEQUENCE: 18
gggcccggat ccttacattc taattttttcc tctgtatttc                          40

<210> SEQ ID NO 19
<211> LENGTH: 52
<212> TYPE: DNA
<213> ORGANISM: artificial
<220> FEATURE:
<223> OTHER INFORMATION: synthetic oligonucleotide primer

<400> SEQUENCE: 19
gggcccctgc agaggagaaa ttaactatga acgaagtggg tatcgtagga ta             52

<210> SEQ ID NO 20
<211> LENGTH: 59
<212> TYPE: DNA
<213> ORGANISM: artificial
<220> FEATURE:
<223> OTHER INFORMATION: synthetic oligonucleotide primer

<400> SEQUENCE: 20
cctacaagtc ccatacacat ttgtatacca gcagtacctg ctttacaagc aaattctaa      59

<210> SEQ ID NO 21
<211> LENGTH: 59
<212> TYPE: DNA
<213> ORGANISM: artificial
<220> FEATURE:
<223> OTHER INFORMATION: synthetic oligonucleotide primer

<400> SEQUENCE: 21
ttagaatttg cttgtaaagc aggtactgct ggtatacaaa tgtgtatggg acttgtagg      59

<210> SEQ ID NO 22
<211> LENGTH: 38
<212> TYPE: DNA
<213> ORGANISM: artificial
<220> FEATURE:
<223> OTHER INFORMATION: synthetic oligonucleotide primer

<400> SEQUENCE: 22
gggcccggat ccttacattc taattttttc tctgtatt                             38
```

<210> SEQ ID NO 23
<211> LENGTH: 52
<212> TYPE: DNA
<213> ORGANISM: artificial
<220> FEATURE:
<223> OTHER INFORMATION: synthetic oligonucleotide primer

<400> SEQUENCE: 23
gggcccggat ccaggagaaa ttaactatgc aaagtttaga taagaatttc cg      52

<210> SEQ ID NO 24
<211> LENGTH: 38
<212> TYPE: DNA
<213> ORGANISM: artificial
<220> FEATURE:
<223> OTHER INFORMATION: synthetic oligonucleotide primer

<400> SEQUENCE: 24
gggccctcta gattattgtt gtctaatttc ttgtaaaa                      38

<210> SEQ ID NO 25
<211> LENGTH: 52
<212> TYPE: DNA
<213> ORGANISM: artificial
<220> FEATURE:
<223> OTHER INFORMATION: synthetic oligonucleotide primer

<400> SEQUENCE: 25
gggcccggat ccaggagaaa ttaactatga aattttacga gttgtctcca ga      52

<210> SEQ ID NO 26
<211> LENGTH: 38
<212> TYPE: DNA
<213> ORGANISM: artificial
<220> FEATURE:
<223> OTHER INFORMATION: synthetic oligonucleotide primer

<400> SEQUENCE: 26
gggccctcta gattaatccc gattttcatc ttttgatt                      38

<210> SEQ ID NO 27
<211> LENGTH: 52
<212> TYPE: DNA
<213> ORGANISM: artificial
<220> FEATURE:
<223> OTHER INFORMATION: synthetic oligonucleotide primer

<400> SEQUENCE: 27
gggcccggat ccaggagaaa ttaactatgg aaaataacgt taatattgaa ga      52

<210> SEQ ID NO 28
<211> LENGTH: 38
<212> TYPE: DNA
<213> ORGANISM: artificial
<220> FEATURE:
<223> OTHER INFORMATION: synthetic oligonucleotide primer

<400> SEQUENCE: 28
gggccctcta gattatcttc caagttcaga atgcgctt                      38

<210> SEQ ID NO 29
<211> LENGTH: 52
<212> TYPE: DNA
<213> ORGANISM: artificial
<220> FEATURE:
<223> OTHER INFORMATION: synthetic oligonucleotide primer -continued

<400> SEQUENCE: 29
gggcccggat ccaggagaaa ttaactatga acaatataaa aaataataat ga        52

<210> SEQ ID NO 30
<211> LENGTH: 38
<212> TYPE: DNA
<213> ORGANISM: artificial
<220> FEATURE:
<223> OTHER INFORMATION: synthetic oligonucleotide primer

<400> SEQUENCE: 30
gggccctcta gattaccttc ctaattccga atgtgctt                        38

<210> SEQ ID NO 31
<211> LENGTH: 38
<212> TYPE: DNA
<213> ORGANISM: artificial
<220> FEATURE:
<223> OTHER INFORMATION: synthetic oligonucleotide primer

<400> SEQUENCE: 31
gggcccggta ccatggaaca ctcgggtttc cagccgga                        38

<210> SEQ ID NO 32
<211> LENGTH: 38
<212> TYPE: DNA
<213> ORGANISM: artificial
<220> FEATURE:
<223> OTHER INFORMATION: synthetic oligonucleotide primer

<400> SEQUENCE: 32
gggcccaagc ttttacccct tgttcatgcg ctcacgca                        38

<210> SEQ ID NO 33
<211> LENGTH: 38
<212> TYPE: DNA
<213> ORGANISM: artificial
<220> FEATURE:
<223> OTHER INFORMATION: synthetic oligonucleotide primer

<400> SEQUENCE: 33
gggcccggta ccatggctga actcatccat tccacaat                        38

<210> SEQ ID NO 34
<211> LENGTH: 40
<212> TYPE: DNA
<213> ORGANISM: artificial
<220> FEATURE:
<223> OTHER INFORMATION: synthetic oligonucleotide primer

<400> SEQUENCE: 34
gggcccaagc ttttattgac ttgatgataa gttgaacatt                      40

<210> SEQ ID NO 35
<211> LENGTH: 38
<212> TYPE: DNA
<213> ORGANISM: artificial
<220> FEATURE:
<223> OTHER INFORMATION: synthetic oligonucleotide primer

<400> SEQUENCE: 35
gggcccggta ccatgacgat gcaggccgag tcctctcc                        38

<210> SEQ ID NO 36

<211> LENGTH: 38
<212> TYPE: DNA
<213> ORGANISM: artificial
<220> FEATURE:
<223> OTHER INFORMATION: synthetic oligonucleotide primer

<400> SEQUENCE: 36
gggcccaagc ttttaggccg tcctggattc gctgagtt                    38

<210> SEQ ID NO 37
<211> LENGTH: 38
<212> TYPE: DNA
<213> ORGANISM: artificial
<220> FEATURE:
<223> OTHER INFORMATION: synthetic oligonucleotide primer

<400> SEQUENCE: 37
gggcccggta ccatggatat cattggcgga caacatct                    38

<210> SEQ ID NO 38
<211> LENGTH: 38
<212> TYPE: DNA
<213> ORGANISM: artificial
<220> FEATURE:
<223> OTHER INFORMATION: synthetic oligonucleotide primer

<400> SEQUENCE: 38
gggcccaagc ttttatttca gattctttct aattattt                    38

<210> SEQ ID NO 39
<211> LENGTH: 38
<212> TYPE: DNA
<213> ORGANISM: artificial
<220> FEATURE:
<223> OTHER INFORMATION: synthetic oligonucleotide primer

<400> SEQUENCE: 39
gggcccggta ccatgctttt tacaaacgat acccttgg                    38

<210> SEQ ID NO 40
<211> LENGTH: 59
<212> TYPE: DNA
<213> ORGANISM: artificial
<220> FEATURE:
<223> OTHER INFORMATION: synthetic oligonucleotide primer

<400> SEQUENCE: 40
tggctgtact ctgcaataaa catggttggc accccataaa gggcagtaca cttttcttt    59

<210> SEQ ID NO 41
<211> LENGTH: 59
<212> TYPE: DNA
<213> ORGANISM: artificial
<220> FEATURE:
<223> OTHER INFORMATION: synthetic oligonucleotide primer

<400> SEQUENCE: 41
aaagaaaagt gtactgccct ttatggggtg ccaaccatgt ttattgcaga gtacagcca    59

<210> SEQ ID NO 42
<211> LENGTH: 38
<212> TYPE: DNA
<213> ORGANISM: artificial
<220> FEATURE:
<223> OTHER INFORMATION: synthetic oligonucleotide primer

<400> SEQUENCE: 42

```
gggcccaagc ttttataatt cttccgtttc tttttttca                            38

<210> SEQ ID NO 43
<211> LENGTH: 52
<212> TYPE: DNA
<213> ORGANISM: artificial
<220> FEATURE:
<223> OTHER INFORMATION: synthetic oligonucleotide primer

<400> SEQUENCE: 43
gggcccgcta gcaggagaaa ttaactatga ttatcaaacc gatgattcgc ag            52

<210> SEQ ID NO 44
<211> LENGTH: 38
<212> TYPE: DNA
<213> ORGANISM: artificial
<220> FEATURE:
<223> OTHER INFORMATION: synthetic oligonucleotide primer

<400> SEQUENCE: 44
gggcccggat ccttaaacaa cgtccatgcg ctcgacat                            38

<210> SEQ ID NO 45
<211> LENGTH: 52
<212> TYPE: DNA
<213> ORGANISM: artificial
<220> FEATURE:
<223> OTHER INFORMATION: synthetic oligonucleotide primer

<400> SEQUENCE: 45
gggcccaagc ttaggagaaa ttaactatga gcaccgaggc tcatcctact gt            52

<210> SEQ ID NO 46
<211> LENGTH: 38
<212> TYPE: DNA
<213> ORGANISM: artificial
<220> FEATURE:
<223> OTHER INFORMATION: synthetic oligonucleotide primer

<400> SEQUENCE: 46
gggcccgtcg acttacaact tgctcgggcg ccattgcg                            38

<210> SEQ ID NO 47
<211> LENGTH: 52
<212> TYPE: DNA
<213> ORGANISM: artificial
<220> FEATURE:
<223> OTHER INFORMATION: synthetic oligonucleotide primer

<400> SEQUENCE: 47
gggcccgtcg acaggagaaa ttaactatgc catttgttaa ggactttaag cc            52

<210> SEQ ID NO 48
<211> LENGTH: 60
<212> TYPE: DNA
<213> ORGANISM: artificial
<220> FEATURE:
<223> OTHER INFORMATION: synthetic oligonucleotide primer

<400> SEQUENCE: 48
gagcctttcg ttttatttga tgcctctaga gctagcttaa ttttgtccc aaccgagttt     60

<210> SEQ ID NO 49
<211> LENGTH: 52
<212> TYPE: DNA
```

```
<213> ORGANISM: artificial
<220> FEATURE:
<223> OTHER INFORMATION: synthetic oligonucleotide primer

<400> SEQUENCE: 49
gggcccgtcg acaggagaaa ttaactatgc catttgtaaa aggttttgag cc         52

<210> SEQ ID NO 50
<211> LENGTH: 60
<212> TYPE: DNA
<213> ORGANISM: artificial
<220> FEATURE:
<223> OTHER INFORMATION: synthetic oligonucleotide primer

<400> SEQUENCE: 50
gagcctttcg ttttatttga tgcctctaga gctagcttag ttcttgttcc aacctaaatc    60

<210> SEQ ID NO 51
<211> LENGTH: 52
<212> TYPE: DNA
<213> ORGANISM: artificial
<220> FEATURE:
<223> OTHER INFORMATION: synthetic oligonucleotide primer

<400> SEQUENCE: 51
gggcccgtcg acaggagaaa ttaactatgg ccagaaaatt atttacacct at         52

<210> SEQ ID NO 52
<211> LENGTH: 60
<212> TYPE: DNA
<213> ORGANISM: artificial
<220> FEATURE:
<223> OTHER INFORMATION: synthetic oligonucleotide primer

<400> SEQUENCE: 52
gagcctttcg ttttatttga tgcctctaga gctagcttac cagcctcttt cgtattgaac    60

<210> SEQ ID NO 53
<211> LENGTH: 59
<212> TYPE: DNA
<213> ORGANISM: artificial
<220> FEATURE:
<223> OTHER INFORMATION: synthetic oligonucleotide primer

<400> SEQUENCE: 53
ttccgtcctt ttcatgagaa gaatacatgt ccattggcga catgacaatg cggttttt      59

<210> SEQ ID NO 54
<211> LENGTH: 59
<212> TYPE: DNA
<213> ORGANISM: artificial
<220> FEATURE:
<223> OTHER INFORMATION: synthetic oligonucleotide primer

<400> SEQUENCE: 54
aaaaaaccgc attgtcatgt cgccaatgga catgtattct tctcatgaaa aggacggaa     59

<210> SEQ ID NO 55
<211> LENGTH: 59
<212> TYPE: DNA
<213> ORGANISM: artificial
<220> FEATURE:
<223> OTHER INFORMATION: synthetic oligonucleotide primer

<400> SEQUENCE: 55
cgctccaaat gcctaagtct tggtcagtcg ttcgtccttg agggttaacc gctgacgcc     59
```

<210> SEQ ID NO 56
<211> LENGTH: 59
<212> TYPE: DNA
<213> ORGANISM: artificial
<220> FEATURE:
<223> OTHER INFORMATION: synthetic oligonucleotide primer

<400> SEQUENCE: 56
ggcgtcagcg gttaaccctc aaggacgaac gactgaccaa gacttaggca tttggagcg    59

<210> SEQ ID NO 57
<211> LENGTH: 52
<212> TYPE: DNA
<213> ORGANISM: artificial
<220> FEATURE:
<223> OTHER INFORMATION: synthetic oligonucleotide primer

<400> SEQUENCE: 57
gggcccaagc ttaggagaaa ttaactatgc caagaatctt ccgttctgcc ga            52

<210> SEQ ID NO 58
<211> LENGTH: 38
<212> TYPE: DNA
<213> ORGANISM: artificial
<220> FEATURE:
<223> OTHER INFORMATION: synthetic oligonucleotide primer

<400> SEQUENCE: 58
gggcccgcta gcttagaagt aatagcggct gatggtct                            38

<210> SEQ ID NO 59
<211> LENGTH: 52
<212> TYPE: DNA
<213> ORGANISM: artificial
<220> FEATURE:
<223> OTHER INFORMATION: synthetic oligonucleotide primer

<400> SEQUENCE: 59
gggcccaagc ttaggagaaa ttaactatgc gtaccatcgc atcgctggaa ga            52

<210> SEQ ID NO 60
<211> LENGTH: 38
<212> TYPE: DNA
<213> ORGANISM: artificial
<220> FEATURE:
<223> OTHER INFORMATION: synthetic oligonucleotide primer

<400> SEQUENCE: 60
gggcccgcta gcttacccgt agcggcgcgt gatcgact                            38

<210> SEQ ID NO 61
<211> LENGTH: 52
<212> TYPE: DNA
<213> ORGANISM: artificial
<220> FEATURE:
<223> OTHER INFORMATION: synthetic oligonucleotide primer

<400> SEQUENCE: 61
gggcccaagc ttaggagaaa ttaactatga gccaggtcca gaacattccc ta            52

<210> SEQ ID NO 62
<211> LENGTH: 38
<212> TYPE: DNA
<213> ORGANISM: artificial
<220> FEATURE:

| | |
|---|---|
| <223> OTHER INFORMATION: synthetic oligonucleotide primer | |
| <400> SEQUENCE: 62 | |
| gggcccgcta gcttagccga tgctgatcgg cggcagtt | 38 |